(12) United States Patent
Kashiki et al.

(10) Patent No.: US 9,889,070 B2
(45) Date of Patent: Feb. 13, 2018

(54) CURABLE COMPOSITION

(71) Applicant: KURARAY NORITAKE DENTAL INC., Kurashiki-shi (JP)

(72) Inventors: Nobusuke Kashiki, Tainai (JP); Kenji Suzuki, Tainai (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 0 days.

(21) Appl. No.: 14/779,134

(22) PCT Filed: Mar. 19, 2014

(86) PCT No.: PCT/JP2014/001594
§ 371 (c)(1),
(2) Date: Sep. 22, 2015

(87) PCT Pub. No.: WO2014/156077
PCT Pub. Date: Oct. 2, 2014

(65) Prior Publication Data
US 2016/0051450 A1 Feb. 25, 2016

(30) Foreign Application Priority Data
Mar. 28, 2013 (JP) ................. 2013-070195

(51) Int. Cl.
| | | |
|---|---|---|
| C08L 33/10 | (2006.01) | |
| C08L 33/26 | (2006.01) | |
| C08F 22/10 | (2006.01) | |
| C08F 22/38 | (2006.01) | |
| A61K 6/00 | (2006.01) | |
| A61K 6/083 | (2006.01) | |
| C09J 4/06 | (2006.01) | |

(52) U.S. Cl.
CPC ............ *A61K 6/0047* (2013.01); *A61K 6/083* (2013.01); *C08F 22/10* (2013.01); *C08F 22/38* (2013.01); *C09J 4/06* (2013.01)

(58) Field of Classification Search
None
See application file for complete search history.

(56) References Cited

U.S. PATENT DOCUMENTS

| | | | | |
|---|---|---|---|---|
| 3,625,930 A | | 12/1971 | Toback et al. | |
| 4,174,311 A | * | 11/1979 | Nakano | C09D 4/00 524/853 |
| 4,467,079 A | * | 8/1984 | Hechenberger | C09J 4/00 526/204 |
| 4,554,301 A | * | 11/1985 | Dohi | C08F 290/048 524/210 |
| 4,596,857 A | * | 6/1986 | Doi | C09J 4/06 524/417 |
| 4,656,211 A | * | 4/1987 | Nasu | C08G 18/8061 427/385.5 |
| 4,898,899 A | * | 2/1990 | Isobe | C09J 4/00 524/90 |
| 5,328,947 A | * | 7/1994 | Taguchi | C08G 18/672 524/850 |
| 5,698,651 A | * | 12/1997 | Kawasaki | C08F 210/18 524/554 |
| 5,863,989 A | * | 1/1999 | Taguchi | C08F 290/062 525/245 |
| RE36,140 E | | 3/1999 | Taguchi et al. | |
| 6,232,431 B1 | * | 5/2001 | Hosoki | C08F 283/006 528/196 |
| 6,420,467 B1 | * | 7/2002 | Ohtsuka | C08F 290/04 428/463 |
| 2003/0134933 A1 | | 7/2003 | Jin et al. | |
| 2003/0166740 A1 | * | 9/2003 | Mitra | A61K 6/0023 523/115 |
| 2007/0040151 A1 | * | 2/2007 | Utterodt | A61K 6/0017 252/182.13 |
| 2010/0036075 A1 | * | 2/2010 | Ishino | A61K 6/0023 526/320 |

(Continued)

FOREIGN PATENT DOCUMENTS

| | | |
|---|---|---|
| CN | 1603349 A | 4/2005 |
| GB | 715382 | 9/1954 |

(Continued)

OTHER PUBLICATIONS

Extended European Search Report dated Aug. 22, 2016 in Patent Application No. 14775348.7.
International Search Report dated Jun. 10, 2014 in PCT/JP2014/001594 filed Mar. 19, 2014.
Xu Xiaoqiu, et al., "Process and Formulation for Super Absorbent Resin" Chemical Industry Press & Materials Science and Engineering Publishing Center, 2004, pp. 286-289 ( with English translation).

*Primary Examiner* — Peter A Salamon
(74) *Attorney, Agent, or Firm* — Oblon, McClelland, Maier & Neustadt, L.L.P.

(57) ABSTRACT

The present invention provides a novel curable composition in which a reaction is caused to occur between a hydroperoxide and a thiourea compound to initiate polymerization of a radical polymerizable monomer and which has excellent adhesive properties, moderate curability, and excellent long-term storage stability. The present invention relates to a curable composition (A) containing: a radical polymerizable monomer (a1) having no acidic group; a hydroperoxide compound (a2); and at least one cyclic thiourea compound (a3) selected from the group consisting of a substituted ethylenethiourea compound (a3-1), a substituted propylenethiourea compound (a3-2), and a substituted butylenethiourea compound (a3-3) each having a specific structure with a cyclic structure moiety into which a substituent is introduced.

13 Claims, No Drawings

(56) References Cited

U.S. PATENT DOCUMENTS

| | | | |
|---|---|---|---|
| 2010/0311864 A1* | 12/2010 | Arita | A61K 6/0029 523/118 |
| 2012/0059083 A1* | 3/2012 | Tokui | A61K 6/0023 523/118 |
| 2013/0236670 A1* | 9/2013 | Hamaguchi | B32B 25/08 428/36.8 |
| 2013/0237667 A1* | 9/2013 | Brandau | C08C 19/38 525/123 |
| 2016/0051450 A1* | 2/2016 | Kashiki | C09J 4/06 523/118 |

FOREIGN PATENT DOCUMENTS

| | | | |
|---|---|---|---|
| GB | 715382 A * | 9/1954 | C08G 4/28 |
| JP | 48 43939 | 12/1973 | |
| JP | 2 187401 | 7/1990 | |
| JP | 2007 56020 | 3/2007 | |
| JP | 2009 292762 | 12/2009 | |
| JP | 2010 280630 | 12/2010 | |

* cited by examiner

CURABLE COMPOSITION

TECHNICAL FIELD

The present invention relates to a curable composition in which a reaction is caused to occur between an oxidizing agent and a reducing agent to initiate polymerization. More specifically, the present invention relates to a curable composition having excellent adhesive properties, moderate curability, and excellent long-term storage stability, and particularly to a curable composition suitable for dental applications.

BACKGROUND ART

Curable compositions containing polymerizable monomers and radical polymerization initiators are widely used in various applications such as coating materials, printing materials, adhesive materials, modeling materials, sealing materials, and dental materials. Among these, in dental applications, curable compositions containing, as polymerizable monomers, (meth)acrylate polymerizable monomers or (meth)acrylamide polymerizable monomers are in practical use as dental materials such as dental cements, dental adhesives, dental composite resins, dental autopolymerizing resins, etc.

A type of common radical polymerization initiator is a polymerization initiator composed of a combination of an oxidizing agent and a reducing agent. When an oxidizing agent and a reducing agent are mixed, a so-called redox reaction occurs to generate radicals, so that the generated radicals initiate a polymerization reaction to promote curing of a composition.

A specific example of the combination is, for example, a combination of a benzolyl peroxide as an oxidizing agent and an amine compound as a reducing agent. However, benzoyl peroxides have the disadvantage of being hard to handle because, due to their low thermal stability and poor storage stability, they must be kept refrigerated. On the other hand, amine compounds are easily converted into colored substances by chemical changes. Due to their susceptibility to coloring, amine compounds have the disadvantage of being hard to use in applications that require aesthetic value such as dental applications.

To address this problem, Patent Literatures 1 and 2 propose, as an improved radical polymerization initiator free of these disadvantages, a combination of a hydroperoxide and an acyclic thiourea compound. Patent Literature 3 proposes, as a radical polymerization initiator, a combination of a hydroperoxide and a cyclic thiourea compound having an unsubstituted cyclic structure. Hydroperoxides are more thermally stable than benzoyl peroxides or the like and are advantageous in storage stability. Unlike amine compounds, thiourea compounds are resistant to coloring.

CITATION LIST

Patent Literature

Patent Literature 1: US 2003/0134933 A1
Patent Literature 2: JP 2007-56020 A
Patent Literature 3: JP 2009-292762 A

SUMMARY OF INVENTION

Technical Problem

In order to improve the reliability of dental materials, they are required to have high bond strength to tooth structures and dental restorative materials, particularly high bond strength to dentin. From a practical point of view, dental materials are required to have moderate curability, that is, a moderately high cure rate and a moderately long working time. Dental materials are further required to have storage stability high enough to maintain its curability in long-term storage.

Solution to Problem

As a result of their studies, the present inventors have found that when a combination of a hydroperoxide and an acyclic thiourea compound described in Patent Literatures 1 and 2 is used in a dental composition, the curability of the composition significantly varies depending on the type of the thiourea compound used and the reaction conditions such as a polymerization accelerator, etc., which makes it difficult to provide the properties suitable for use as a dental composition. For example, the curability of the dental composition is insufficient, or even if the composition has moderate curability and adhesive properties, the curability decreases after long-term storage, resulting in poor storage stability. The present inventors have also found that when a combination of a hydroperoxide and a cyclic thiourea compound having an unsubstituted cyclic structure described in Patent Literature 3 is used in a dental composition, the curability of the composition decreases after long-term storage, resulting in poor storage stability. The present inventors have further found that this composition exhibits very low adhesive properties under acidic conditions.

Accordingly, it is an object of the present invention to provide a novel curable composition in which a reaction is caused to occur between a hydroperoxide and a thiourea compound to initiate polymerization of a radical polymerizable monomer and which has excellent adhesive properties, moderate curability, and excellent long-term storage stability.

As a result of intensive studies to solve the above problems, the present inventors have found that the above problems can be solved by a curable composition containing a radical polymerizable monomer, a hydroperoxide as an oxidizing agent of a polymerization initiator, and a thiourea compound as a reducing agent of the polymerization initiator, in which the thiourea compound is at least one selected from the group consisting of a substituted ethylenethiourea compound, a substituted propylenethiourea compound, and a substituted butylenethiourea compound each having a specific structure. Based on these findings, the present inventors have completed this invention.

The present invention relates to a curable composition (A) containing: a radical polymerizable monomer (a1) having no acidic group; a hydroperoxide compound (a2); and at least one cyclic thiourea compound (a3) selected from the group consisting of a substituted ethylenethiourea compound (a3-1), a substituted propylenethiourea compound (a3-2), and a substituted butylenethiourea compound (a3-3).

The substituted ethylenethiourea compound (a3-1) has a structure represented by the following formula (I):

In this formula, $R_1$, $R_2$, $R_3$, $R_4$, $R_5$, and $R_6$ are each independently a hydrogen atom, an optionally substituted alkyl group, an optionally substituted cycloalkyl group, an optionally substituted alkoxy group, an optionally substituted aryl group, an optionally substituted acyl group, an optionally substituted alkenyl group, an optionally substituted aralkyl group, or an optionally substituted monovalent heterocyclic group containing an oxygen atom, a sulfur atom or a nitrogen atom (except when $R_1$, $R_2$, $R_3$, $R_4$, $R_5$, and $R_6$ are all hydrogen atoms), and $R_4$ and $R_5$, together with carbon atoms to which $R_4$ and $R_5$ are attached, may form an optionally substituted ring.

The substituted propylenethiourea compound (a3-2) has a structure represented by the following formula (II):

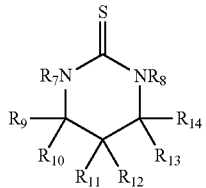

(II)

In this formula, $R_7$, $R_8$, $R_9$, $R_{10}$, $R_{11}$, $R_{12}$, $R_{13}$, and $R_{14}$ are each independently a hydrogen atom, an optionally substituted alkyl group, an optionally substituted cycloalkyl group, an optionally substituted alkoxy group, an optionally substituted aryl group, an optionally substituted acyl group, an optionally substituted alkenyl group, an optionally substituted aralkyl group, or an optionally substituted monovalent heterocyclic group containing an oxygen atom, a sulfur atom or a nitrogen atom (except when $R_7$, $R_8$, $R_9$, $R_{10}$, $R_{11}$, $R_{12}$, $R_{13}$, and $R_{14}$ are all hydrogen atoms), and $R_9$ and $R_{11}$, or $R_9$ and $R_{13}$, together with carbon atoms to which $R_9$ and $R_{11}$, or $R_9$ and $R_{13}$ are attached, may form an optionally substituted ring.

The substituted butylenethiourea compound (a3-3) has a structure represented by the following formula (III):

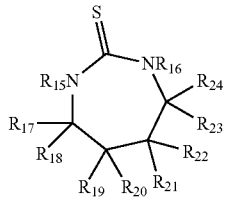

(III)

In this formula, $R_{15}$, $R_{16}$, $R_{17}$, $R_{18}$, $R_{19}$, $R_{20}$, $R_{21}$, $R_{22}$, $R_{23}$, and $R_{24}$ are each independently a hydrogen atom, an optionally substituted alkyl group, an optionally substituted cycloalkyl group, an optionally substituted alkoxy group, an optionally substituted aryl group, an optionally substituted acyl group, an optionally substituted alkenyl group, an optionally substituted aralkyl group, or an optionally substituted monovalent heterocyclic group containing an oxygen atom, a sulfur atom or a nitrogen atom (except when $R_{15}$, $R_{16}$, $R_{17}$, $R_{18}$, $R_{19}$, $R_{20}$, $R_{21}$, $R_{22}$, $R_{23}$, and $R_{24}$ are all hydrogen atoms), and $R_{17}$ and $R_{19}$, $R_{17}$ and $R_{21}$, $R_{17}$ and $R_{23}$, or $R_{19}$ and $R_{21}$, together with carbon atoms to which $R_{17}$ and $R_{19}$, $R_{17}$ and $R_{21}$, $R_{17}$ and $R_{23}$, or $R_{19}$ and $R_{21}$ are attached, may form an optionally substituted ring.

In a specific embodiment of the present invention, the curable composition (A) further contains a filler (a4).

In a specific embodiment of the present invention, the radical polymerizable monomer (a1) having no acidic group is a (meth)acrylate polymerizable monomer and/or a (meth)acrylamide polymerizable monomer.

In a specific embodiment of the present invention, the curable composition (A) further contains an acidic group-containing radical polymerizable monomer (a5).

In a specific embodiment of the present invention, the curable composition (A) further contains a vanadium compound (a6) and/or a copper compound (a7).

In a preferred embodiment of the present invention, the cyclic thiourea compound (a3) is at least one selected from the group consisting of 4-methyl-2-imidazolidinethione, 4,4-dimethyl-2-imidazolidinethione, 4-ethyl-2-imidazolidinethione, and 4,4-diethyl-2-imidazolidinethione.

The curable composition of the present invention is suitable for use in dental applications.

The present invention also relates to an adhesive kit including: a pretreatment agent (B) containing an acidic group-containing radical polymerizable monomer (b1), a polymerization accelerator (b2), a solvent (b3), and a hydrophilic radical polymerizable monomer (b4) having no acidic group; and the curable composition (A) described above.

In a specific embodiment of the adhesive kit of the present invention, the polymerization accelerator (b2) is a vanadium compound (b2-1) and/or a copper compound (b2-2).

The adhesive kit of the present invention is suitable for use in dental applications.

Advantageous Effects of Invention

The curable composition of the present invention contains a hydroperoxide and a thiourea compound as a radical polymerization initiator but has excellent adhesive properties, moderate curability, and excellent long-term storage stability.

The present invention is a curable composition (A) containing: a radical polymerizable monomer (a1) having no acidic group; a hydroperoxide compound (a2) as an oxidizing agent of a polymerization initiator; and a cyclic thiourea compound (a3) as a reducing agent of the polymerization initiator, and this curable composition (A) is characterized primarily in that one selected from the group consisting of a substituted ethylenethiourea compound (a3-1), a substituted propylenethiourea compound (a3-2), and a substituted butylenethiourea compound (a3-3) each having a specific structure is used as the cyclic thiourea compound (a3).

DESCRIPTION OF EMBODIMENTS

The substituted ethylenethiourea compound (a3-1) used in the present invention has a structure represented by the following formula (I):

(I)

In this formula, $R_1$, $R_2$, $R_3$, $R_4$, $R_5$, and $R_6$ are each independently a hydrogen atom, an optionally substituted alkyl group, an optionally substituted cycloalkyl group, an optionally substituted alkoxy group, an optionally substituted aryl group, an optionally substituted acyl group, an optionally substituted alkenyl group, an optionally substituted aralkyl group, or an optionally substituted monovalent heterocyclic group containing an oxygen atom, a sulfur atom or a nitrogen atom (except when $R_1$, $R_2$, $R_3$, $R_4$, $R_5$, and $R_6$ are all hydrogen atoms), and $R_4$ and $R_5$, together with carbon atoms to which $R_4$ and $R_5$ are attached, may form an optionally substituted ring.

The substituted propylenethiourea compound (a3-2) used in the present invention has a structure represented by the following formula (II):

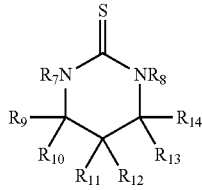

(II)

In this formula, $R_7$, $R_8$, $R_9$, $R_{10}$, $R_{11}$, $R_{12}$, $R_{13}$, and $R_{14}$ are each independently a hydrogen atom, an optionally substituted alkyl group, an optionally substituted cycloalkyl group, an optionally substituted alkoxy group, an optionally substituted aryl group, an optionally substituted acyl group, an optionally substituted alkenyl group, an optionally substituted aralkyl group, or an optionally substituted monovalent heterocyclic group containing an oxygen atom, a sulfur atom or a nitrogen atom (except when $R_7$, $R_8$, $R_9$, $R_{10}$, $R_{11}$, $R_{12}$, $R_{13}$, and $R_{14}$ are all hydrogen atoms), and $R_9$ and $R_{11}$, or $R_9$ and $R_{13}$, together with carbon atoms to which $R_9$ and $R_{11}$, or $R_9$ and $R_{13}$ are attached, may form an optionally substituted ring.

The substituted butylenethiourea compound (a3-3) used in the present invention has a structure represented by the following formula (III):

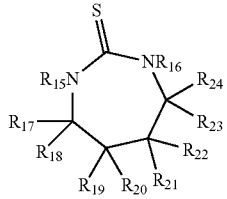

(III)

In this formula, $R_{15}$, $R_{16}$, $R_{17}$, $R_{18}$, $R_{19}$, $R_{20}$, $R_{21}$, $R_{22}$, $R_{23}$, and $R_{24}$ are each independently a hydrogen atom, an optionally substituted alkyl group, an optionally substituted cycloalkyl group, an optionally substituted alkoxy group, an optionally substituted aryl group, an optionally substituted acyl group, an optionally substituted alkenyl group, an optionally substituted aralkyl group, or an optionally substituted monovalent heterocyclic group containing an oxygen atom, a sulfur atom or a nitrogen atom (except when $R_{15}$, $R_{16}$, $R_{17}$, $R_{18}$, $R_{19}$, $R_{20}$, $R_{21}$, $R_{22}$, $R_{23}$, and $R_{24}$ are all hydrogen atoms), and $R_{17}$ and $R_{19}$, $R_{17}$ and $R_{21}$, $R_{17}$ and $R_{23}$, or $R_{19}$ and $R_{21}$, together with carbon atoms to which $R_{17}$ and $R_{19}$, $R_{17}$ and $R_{21}$, $R_{17}$ and $R_{23}$, or $R_{19}$ and $R_{21}$ are attached, may form an optionally substituted ring.

The cyclic thiourea compound (a3) having any of these structures has a planar molecular structure. Therefore, its reaction activity with a hydroperoxide can be increased, and as a result, both high adhesive properties and moderate curability of the curable composition can be achieved.

In addition, the cyclic structure moiety of the cyclic thiourea compound (a3) has at least one substituent. Surprisingly, a cyclic thiourea compound having a substituent introduced into its cyclic structure moiety has the effect of maintaining its curability almost unchanged even after long-term storage at room temperature or higher. Presumably, this is because the solubility of the cyclic thiourea compound in the radical polymerizable monomer (in particular, a (meth)acrylate polymerizable monomer or a (meth)acrylamide polymerizable monomer) is significantly improved by introducing a substituent into the cyclic structure moiety of the cyclic thiourea compound, and even if the composition is stored for a long time, the cyclic thiourea compound serving as a reducing agent is still uniformly dispersed in the composition without being separated from the radical polymerizable monomer and contributes to initiation of polymerization of the polymerizable monomer. Since this cyclic thiourea compound has significantly improved solubility in the radical polymerizable monomer, the content of this cyclic thiourea compound in the composition can be increased compared with a cyclic thiourea compound having no substituent in its cyclic structure moiety, which produces the effect that the curability of the composition can be easily controlled. In addition, the use of the cyclic thiourea compound (a3) produces the effect that both high adhesive properties and moderate curability can be achieved under a wider range of reaction conditions (such as a catalyst and the presence of acid) than the use of a conventional thiourea compound.

The essential components of the curable composition (A) of the present invention, i.e., the radical polymerizable monomer (a1) having no acidic group, the hydroperoxide compound (a2), and the cyclic thiourea compound (a3) having the above-described specific structure are described below.

The radical polymerizable monomer (a1) having no acidic group is not particularly limited as long as it is a radical polymerizable monomer not having an acidic group such as a phosphate group, a pyrophosphate group, a thiophosphate group, a phosphonate group, a sulfonate group, or a carboxylate group, but having a polymerizable group. Preferred examples of such a polymerizable monomer include polymerizable monomers having an acryloyl group or a methacryloyl group, that is, (meth)acrylate polymerizable monomers and (meth)acrylamide polymerizable monomers. As used here in this description, the term "(meth)acryl" refers to both "methacryl" and "acryl".

Specific examples of these polymerizable monomers are as follows.

Examples of monofunctional aliphatic polymerizable monomers include methyl (meth)acrylate, ethyl(meth)acrylate, propyl(meth)acrylate, butyl (meth)acrylate, isobutyl (meth)acrylate, lauryl(meth)acrylate, 2,3-dibromopropyl (meth)acrylate, methoxypolyethylene glycol(meth)acrylate, glycidyl(meth)acrylate, 2-hydroxyethyl(meth)acrylate (commonly known as "HEMA"), 3-hydroxypropyl(meth) acrylate, 3-chloro-2-hydroxypropyl(meth)acrylate, tetrahydrofurfuryl(meth)acrylate, (meth)acryloyl morpholine, and diethyl(meth)acrylamide.

Examples of difunctional aliphatic polymerizable monomers include erythritol di(meth)acrylate, sorbitol di(meth)acrylate, mannitol di(meth)acrylate, pentaerythritol di(meth)acrylate, dipentaerythritol di(meth)acrylate, glycerol di(meth)acrylate, 1,2-bis(3-methacryloyloxy-2-hydroxypropyloxy)ethane, ethylene glycol di(meth)acrylate, diethylene glycol di(meth)acrylate, triethylene glycol di(meth)acrylate, polyethylene glycol di(meth)acrylate, propylene glycol di(meth)acrylate, butylene glycol di(meth)acrylate, neopentyl glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, 2,2,4-trimethylhexamethylene bis(2-carbamoyloxyethyl)dimethacrylate (commonly known as "UDMA"), tricyclodecanedimethanol di(meth)acrylate, ethylenebis(meth)acrylamide, propylenebis(meth)acrylamide, butylenebis(meth)acrylamide, N,N'-(dimethyl)ethylenebis(meth)acrylamide, N,N'-diethyl-1,3-propylenebis(meth)acrylamide, bis[2-(2-methyl-(meth)acrylamino)ethoxycarbonyl]hexamethylenediamine, and 2,2,4-trimethylhexamethylene-1,6-bis(meth)acrylamide.

Examples of tri- or higher-functional aliphatic polymerizable monomers include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol tri(meth)acrylate, dipentaerythritol tetra(meth)acrylate, dipentaerythritol penta(meth)acrylate, N,N-(2,2,4-trimethylhexamethylene)bis[2-(aminocarboxy)propane-1,3-diol] tetramethacrylate, and 1,7-diacryloyloxy-2,2,6,6-tetraacryloyloxymethyl-4-oxyheptane.

Examples of monofunctional aromatic polymerizable monomers include benzyl(meth)acrylate, phenoxyethyl (meth)acrylate, phenoxydiethylene glycol(meth)acrylate, phenoxypolyethylene glycol(meth)acrylate, 2-hydroxy-3-phenoxypropyl(meth)acrylate, 2-(meth)acryloyloxyethyl-2-hydroxyethyl phthalate, and neopentyl glycol(meth)acrylate benzoate.

Examples of difunctional aromatic polymerizable monomers include
2,2-bis[4-(3-(meth)acryloyloxy)-2-hydroxypropoxyphenyl] propane (commonly known as "Bis-GMA"), 2,2-bis[4-(4-(meth)acryloyloxy)-3-hydroxybutoxyphenyl]propane,
2,2-bis[4-(4-(meth)acryloyloxy)-2-hydroxybutoxyphenyl] propane,
2,2-bis[4-(5-(meth)acryloyloxy)-4-hydroxypentoxyphenyl] propane,
2,2-bis((meth)acryloyloxyphenyl)propane,
2,2-bis(4-(meth)acryloyloxyethoxyphenyl)propane,
2,2-bis(4-(meth)acryloyloxydiethoxyphenyl)propane,
2,2-bis(4-(meth)acryloyloxytriethoxyphenyl)propane,
2,2-bis(4-(meth)acryloyloxytetraethoxyphenyl)propane,
2,2-bis(4-(meth)acryloyloxypentaethoxyphenyl)propane,
2-(4-(meth)acryloyloxydiethoxyphenyl)-2-(4-(meth)acryloyloxyethoxyphenyl) propane,
2-(4-(meth)acryloyloxydiethoxyphenyl)-2-(4-(meth)acryloyloxytriethoxyphenyl) propane,
2,2-bis(4-(meth)acryloyloxypolyethoxyphenyl)propane,
2-(4-(meth)acryloyloxydipropoxyphenyl)-2-(4-(meth)acryloyloxytriethoxyphenyl) propane,
2,2-bis(4-(meth)acryloyloxypropoxyphenyl)propane,
2,2-bis(4-(meth)acryloyloxydipropoxyphenyl)propane, and
2,2-bis(4-(meth)acryloyloxyisopropoxyphenyl)propane.

Examples of tri- or higher-functional aromatic polymerizable monomers include pentaerythritol tri(meth)acrylate.

Examples of polyfunctional aromatic polymerizable monomers include 1,7-di(meth)acryloyloxy-2,2,6,6-tetra (meth)acryloyloxymethyl-4-oxaheptane, and dipentaerythritol hexa(meth)acrylate.

The hydroperoxide compound (a2) is a component serving as an oxidizing agent of a redox polymerization initiator.

As the hydroperoxide compound (a2), any known hydroperoxide compound can be used without any limitation. The hydroperoxide compound (a2) is preferably a hydroperoxide having one or more hydroperoxide groups (—OOH groups) per molecule, and more preferably a hydroperoxide having a —OOH group bonded to a tertiary carbon atom per molecule.

Specific examples of the hydroperoxide compound (a2) include 1,1,3,3-tetramethylbutyl hydroperoxide, cumene hydroperoxide, t-butyl hydroperoxide, t-amyl hydroperoxide, p-menthane hydroperoxide, p-isopropylcumyl hydroperoxide, diisopropylbenzene hydroperoxide, and diisopropylbenzene dihydroperoxide. These can be used alone, or two or more of them can be used in combination. It is preferable to use, among these, cumene hydroperoxide and/or 1,1,3,3-tetramethylbutyl hydroperoxide.

The content of the hydroperoxide compound (a2) in the curable composition (A) is preferably 0.01 to 20 wt. %, more preferably 0.05 to 10 wt. % of the total amount of the curable composition (A). The content of less than 0.01 wt. % may be too low to allow the hydroperoxide compound (a2) to act as a redox polymerization initiator. The content of more than 20 wt. % tends to cause the polymerization of the radical polymerizable monomer in the curable composition (A) to proceed readily, which may cause a decrease in the storage stability of the curable composition (A).

The cyclic thiourea compound (a3) is a component serving as a reducing agent of a redox polymerization initiator. As the cyclic thiourea compound (a3), at least one selected from the group consisting of a substituted ethylenethiourea compound (a3-1), a substituted propylenethiourea compound (a3-2), and a substituted butylenethiourea compound (a3-3) is used.

As the substituted ethylenethiourea compound (a3-1), any compound can be used without any limitation as long as it has a structure represented by the following formula (I):

In this formula, $R_1$, $R_2$, $R_3$, $R_4$, $R_5$, and $R_6$ are each independently a hydrogen atom, an optionally substituted alkyl group, an optionally substituted cycloalkyl group, an optionally substituted alkoxy group, an optionally substituted aryl group, an optionally substituted acyl group, an optionally substituted alkenyl group, an optionally substituted aralkyl group, or an optionally substituted monovalent heterocyclic group containing an oxygen atom, a sulfur atom or a nitrogen atom (except when $R_1$, $R_2$, $R_3$, $R_4$, $R_5$, and $R_6$ are all hydrogen atoms), and $R_4$ and $R_5$, together with carbon atoms to which $R_4$ and $R_5$ are attached, may form an optionally substituted ring.

As the substituted propylenethiourea compound (a3-2), any compound can be used without any limitation as long as it has a structure represented by the following formula (II):

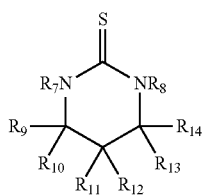

(II)

In this formula, $R_7$, $R_8$, $R_9$, $R_{10}$, $R_{11}$, $R_{12}$, $R_{13}$, and $R_{14}$ are each independently a hydrogen atom, an optionally substituted alkyl group, an optionally substituted cycloalkyl group, an optionally substituted alkoxy group, an optionally substituted aryl group, an optionally substituted acyl group, an optionally substituted alkenyl group, an optionally substituted aralkyl group, or an optionally substituted monovalent heterocyclic group containing an oxygen atom, a sulfur atom or a nitrogen atom (except when $R_7$, $R_8$, $R_9$, $R_{10}$, $R_{11}$, $R_{12}$, $R_{13}$, and $R_{14}$ are all hydrogen atoms), and $R_9$ and $R_{11}$, or $R_9$ and $R_{13}$, together with carbon atoms to which $R_9$ and $R_{11}$, or $R_9$ and $R_{13}$ are attached, may form an optionally substituted ring.

As the substituted butylenethiourea compound (a3-3), any compound can be used without any limitation as long as it has a structure represented by the following formula (III):

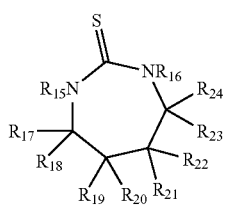

(III)

In this formula, $R_{15}$, $R_{16}$, $R_{17}$, $R_{18}$, $R_{19}$, $R_{20}$, $R_{21}$, $R_{22}$, $R_{23}$, and $R_{24}$ are each independently a hydrogen atom, an optionally substituted alkyl group, an optionally substituted cycloalkyl group, an optionally substituted alkoxy group, an optionally substituted aryl group, an optionally substituted acyl group, an optionally substituted alkenyl group, an optionally substituted aralkyl group, or an optionally substituted monovalent heterocyclic group containing an oxygen atom, a sulfur atom or a nitrogen atom (except when $R_{15}$, $R_{16}$, $R_{17}$, $R_{18}$, $R_{19}$, $R_{20}$, $R_{21}$, $R_{22}$, $R_{23}$, and $R_{24}$ are all hydrogen atoms), and $R_{17}$ and $R_{19}$, $R_{17}$ and $R_{21}$, $R_{17}$ and $R_{23}$, or $R_{19}$ and $R_{21}$, together with carbon atoms to which $R_{17}$ and $R_{19}$, $R_{17}$ and $R_{21}$, $R_{17}$ and $R_{23}$, or $R_{19}$ and $R_{21}$ are attached, may form an optionally substituted ring.

The alkyl group represented by $R_1$ to $R_{24}$ may be either linear or branched, and preferably it has 1 to 12 carbon atoms. Examples of the alkyl group include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, an n-hexyl group, an isohexyl group, an n-heptyl group, an n-octyl group, a 2-ethylhexyl group, an n-nonyl group, and an n-decyl group.

Preferably, the cycloalkyl group represented by $R_1$ to $R_{24}$ has 3 to 10 carbon atoms. Examples of the cycloalkyl group include a cyclopropyl group, a cyclobutyl group, a cyclopentyl group, a cyclohexyl group, a cycloheptenyl group, a cyclooctenyl group, and a cyclononanyl group.

Preferably, the alkoxy group represented by $R_1$ to $R_{24}$ has 3 to 8 carbon atoms. Examples of the alkoxy group include a propoxy group, an isopropoxy group, an n-butoxy group, a t-butoxy group, a pentyloxy group, and a hexyloxy group.

Preferably, the aryl group represented by $R_1$ to $R_{24}$ has 6 to 16 carbon atoms. Examples of the aryl group include a phenyl group, a naphthyl group, an anthryl group, and a phenanthryl group.

Preferably, the acyl group represented by $R_1$ to $R_{24}$ has 1 to 10 carbon atoms. Examples of the acyl group include a formyl group, an acetyl group, a propanoyl group, a butanoyl group, and a benzoyl group.

The alkenyl group represented by $R_1$ to $R_{24}$ may be either linear or branched, and preferably it has 2 to 8 carbon atoms. Examples of the alkenyl group include a vinyl group, an allyl group, a methylvinyl group, a propenyl group, a butenyl group, a pentenyl group, and a hexenyl group.

Preferably, the aralkyl group represented by $R_1$ to $R_{24}$ has 7 to 16 carbon atoms. Such an aralkyl group is, for example, an aryl group substituted by a lower alkyl group (in particular, by an alkyl group having 1 to 6 carbon atoms). Specific examples of the aralkyl group include a methylphenyl group, an ethylphenyl group, a butylphenyl group, a dimethylphenyl group, a dibutylphenyl group, and a methylnaphtyl group.

Preferably, the monovalent heterocyclic group containing an oxygen atom, a sulfur atom or a nitrogen atom and represented by $R_1$ to $R_{24}$ has 4 to 10 carbon atoms. Examples of the monovalent heterocyclic group include a pyridyl group, an imidazolyl group, a piperidyl group, a thienyl group, a thiopyranyl group, a furyl group, and a pyranyl group.

Examples of the optional substituents which may be present on the alkyl group, the cycloalkyl group, the alkoxy group, the acyl group, and the alkenyl group include halogen atoms (such as a chlorine atom and a bromine atom), aryl groups (such as a phenyl group and a naphthyl group), and monovalent heterocyclic groups (such as a pyridyl group and an imidazolyl group). Among these, halogen atoms and aryl groups are preferred. The number of the substituents is preferably 1 to 2. Examples of the optional substituents which may be present on the aryl group, the aralkyl group, and the monovalent heterocyclic group include halogen atoms (such as a chlorine atom and a bromine atom), alkyl groups (such as a methyl group and an ethyl group), alkoxy groups (such as a methoxy group and an ethoxy group), aryl groups (such as a phenyl group and a naphthyl group), and monovalent heterocyclic groups (such as a pyridyl group and an imidazolyl group). Among these, halogen atoms and alkyl groups are preferred. The number of the substituents is preferably 1 to 4, and more preferably 1 to 2.

$R_4$ and $R_5$, $R_9$ and $R_{11}$, $R_9$ and $R_{13}$, $R_{17}$ and $R_{19}$, $R_{17}$ and $R_{21}$, $R_{17}$ and $R_{23}$, or $R_{19}$ and $R_{21}$, together with carbon atoms to which they are attached, may form an optionally substituted ring, and the ring preferably has 4 to 10 carbon atoms. Examples of such a ring include a cyclobutyl ring, a cyclopentyl ring, a cyclohexyl ring, a cycloheptenyl ring, a cyclooctenyl ring, and a cyclononanyl ring. Examples of the optional substituents which may be present on the rings include halogen atoms (such as a chlorine atom and a bromine atom), aryl groups (such as a phenyl group and a naphthyl group), and monovalent heterocyclic groups (such as a pyridyl group and an imidazolyl group).

In terms of curability, adhesive properties, and availability, $R_1$, $R_2$, $R_7$, $R_8$, $R_{15}$, and $R_{16}$ are each preferably a hydrogen atom, an alkyl group, a cycloalkyl group, an aryl group, an alkenyl group, or an aralkyl group, more preferably a hydrogen atom, an alkyl group, or a cycloalkyl group, and even more preferably a hydrogen atom.

In terms of curability, adhesive properties, availability, and solubility in the radical polymerizable monomer, $R_3$ to $R_6$ are each preferably a hydrogen atom, an alkyl group, a cycloalkyl group, an optionally hydrogen atom-substituted aryl group, an alkenyl group, or an aralkyl group, and more preferably a hydrogen atom, an alkyl group, or a cycloalkyl group. Even more preferably, at least one of $R_3$ to $R_6$ is a hydrogen atom and at most three of $R_3$ to $R_6$ are alkyl groups each having 1 to 5 carbon atoms, and most preferably, two of $R_3$ to $R_6$ are hydrogen atoms and the remaining two of $R_3$ to $R_6$ are alkyl groups each having 1 to 2 carbon atoms.

In terms of curability, adhesive properties, availability, and solubility in the radical polymerizable monomer, $R_9$ to $R_{14}$ are each preferably a hydrogen atom, an alkyl group, a cycloalkyl group, an optionally hydrogen atom-substituted aryl group, an alkenyl group, or an aralkyl group, and more preferably a hydrogen atom, an alkyl group, or a cycloalkyl group. Even more preferably, at least three of $R_9$ to $R_{14}$ are hydrogen atoms and at most three of $R_9$ to $R_{14}$ are alkyl groups each having 1 to carbon atoms, and most preferably, four of $R_9$ to $R_{14}$ are hydrogen atoms and the remaining two of $R_9$ to $R_{14}$ are alkyl groups each having 1 to 2 carbon atoms.

In terms of curability, adhesive properties, availability, and solubility in the radical polymerizable monomer, $R_{17}$ to $R_{24}$ are each preferably a hydrogen atom, an alkyl group, a cycloalkyl group, an optionally hydrogen atom-substituted aryl group, an alkenyl group, or an aralkyl group, and more preferably a hydrogen atom, an alkyl group, or a cycloalkyl group. Even more preferably, at least five of $R_{17}$ to $R_{24}$ are hydrogen atoms and at most three of $R_{17}$ to $R_{24}$ are alkyl groups each having 1 to carbon atoms, and most preferably, six of $R_{17}$ to $R_{24}$ are hydrogen atoms and the remaining two of $R_{17}$ to $R_{24}$ are alkyl groups each having 1 to 5 carbon atoms.

The solubility of the above-mentioned cyclic thiourea compound (a3) in triethylene glycol dimethacrylate is preferably 1.0 wt. % or more. The solubility thereof in triethylene glycol dimethacrylate is more preferably 5.0 wt. % or more.

In terms of improvement of bond strength, improvement of curability, availability, and solubility in the radical polymerizable monomer, it is preferable to use, among the above-mentioned examples of the cyclic thiourea compound (a3), at least one selected from the group consisting of 4-methyl-2-imidazolidinethione, 4,4-dimethyl-2-imidazolidinethione, 4,5-dimethyl-2-imidazolidinethione, 4-ethyl-2-imidazolidinethione, 4,4-diethyl-2-imidazolidinethione, 4,5-diethyl-2-imidazolidinethione, 4-methyl-3,4,5,6-tetrahydropyrimidine-2(1H)-thione, 4-ethyl-3,4,5,6-tetrahydropyrimidine-2(1H)-thione, 5-methyl-3,4,5,6-tetrahydropyrimidine-2(1H)-thione, 5-ethyl-3, 4,5,6-tetrahydropyrimidine-2(1H)-thione, 4,4-dimethyl-3,4,5,6-tetrahydropyrimidine-2(1H)-thione, 4,5-dimethyl-3,4,5,6-tetrahydropyrimidine-2(1H)-thione, 4,6-dimethyl-3,4,5,6-tetrahydropyrimidine-2(1H)-thione, 5,5-dimethyl-3,4,5,6-tetrahydropyrimidine-2(1H)-thione, 5-(2-chlorophenyl)-3,4,5,6-tetrahydropyrimidine-2(1H)-thione, and 5,6-dimethyl-3,4,5,6-tetrahydropyrimidine-2 (1H)-thione. It is more preferable to use at least one selected from the group consisting of 4-methyl-2-imidazolidinethione, 4,4-dimethyl-2-imidazolidinethione, 4-ethyl-2-imidazolidinethione, and 4,4-diethyl-2-imidazolidinethione.

The content of the cyclic thiourea compound (a3) is preferably 0.01 to 20 wt. %, more preferably 0.1 to 10 wt. % of the total amount of the curable composition (A). The content of less than 0.01 wt. % may be too low to allow the cyclic thiourea compound (a3) to act as a redox polymerization initiator. The content of more than 20 wt. % causes the curable composition to start curing more rapidly, which may make it difficult to provide a moderately long working time.

Next, optional components for the curable composition (A) of the present invention are described. In the present invention, the curable composition (A) may contain a filler (a4) to prepare dental materials such as a cement and a composite resin.

As the filler (a4) used in the present invention, a filler for use in dental applications is suitably used. Generally, fillers for dental use are classified broadly into organic fillers, inorganic fillers, and organic-inorganic composite fillers. Examples of the material of the organic filler include polymethyl methacrylate, polyethyl methacrylate, methyl methacrylate-ethyl methacrylate copolymer, crosslinked polymethyl methacrylate, crosslinked polyethyl methacrylate, polyamide, polyvinyl chloride, polystyrene, chloroprene rubber, nitrile rubber, ethylene-vinyl acetate copolymer, styrene-butadiene copolymer, acrylonitrile-styrene copolymer, and acrylonitrile-styrene-butadiene copolymer. These fillers can be used alone or in the form of a mixture of two or more thereof. The shape of the particles of the organic filler is not particularly limited, and the particle diameter of the filler can be selected as appropriate for use. In terms of the handling properties of the obtained curable composition and the mechanical strength of the cured product of the curable composition, the average particle diameter of the organic filler is preferably 0.001 to 50 μm, and more preferably 0.001 to 10 μm. In the present description, the average particle diameter of the inorganic particles refers to the average particle diameter of the primary particles of the inorganic particles (average primary particle diameter). In this description, the average particle diameter of the inorganic particles can be determined by laser diffraction scattering or by electron microscopic observation of the particles. Specifically, the laser diffraction scattering method is convenient for particle diameter measurement on particles with a diameter of not less than 0.1 μm, and the electron microscope observation is convenient for particle diameter measurement on ultrafine particles with a diameter of not more than 0.1 μm. To be more specific about the laser diffraction scattering method, for example, the average particle diameter can be measured using a laser diffraction particle size distribution analyzer (SALD-2100, manufactured by Shimadzu Corporation) and using a 0.2% aqueous solution of sodium hexametaphosphate as a dispersion medium. To be more specific about the electron microscope observation, for example, the average particle diameter can be determined by taking a photograph of particles with a transmission electron microscope (H-800NA, manufactured by Hitachi, Ltd.) and measuring the particle diameters of particles (the number of which is 200 or more) observed within a unit area of visual field in the photograph by means of a particle size distribution analysis software of the image analysis type (Macview (Mountech Co., Ltd.)). In this case, the particle diameter of each particle is determined as an arithmetic mean of the maximum and minimum dimensions of the particle, and, from the thus determined particle diameters and the number of the particles, the average primary particle diameter is calculated.

Examples of the material of the inorganic filler include quartz, silica, alumina, silica-titania, silica-titania-barium oxide, silica-zirconia, silica-alumina, lanthanum glass, borosilicate glass, soda glass, barium glass, strontium glass, glass ceramics, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. These also can be used alone or in the form of a mixture of two or more thereof. The shape of the particles of the inorganic filler is not particularly limited, and the particle diameter of the filler can be selected as appropriate for use. In terms of the handling properties of the obtained curable composition and the mechanical strength of the cured product of the curable composition, the average particle diameter of the inorganic filler is preferably 0.001 to 50 μm, and more preferably 0.001 to 10 μm.

The shape of the inorganic filler is, for example, an irregular shape or a spherical shape. In order to increase the mechanical strength of the cured product of the obtained curable composition, it is preferable to use a spherical filler as the inorganic filler. As used herein, the spherical filler refers to a filler whose particles have a round shape having an average aspect ratio (obtained by dividing the dimension of each particle perpendicular to the maximum dimension thereof) of 0.6 or more when observed within a unit area of visual field in a photograph taken by a scanning electron microscope (hereinafter referred to as "SEM"). The average particle diameter of the spherical filler is preferably 0.1 to 5 μm. When the average particle diameter is less than 0.1 μm, the filling rate of the spherical filler in the curable composition (A) decreases, and thereby the mechanical strength of the obtained cured product may also decrease. On the other hand, when the average particle diameter is more than 5 μm, the surface area of the spherical filler decreases and thereby a cured product having high mechanical strength may not be obtained.

In order to adjust the flowability of the curable composition (A), the inorganic filler may be surface-treated before use with a commonly-known surface treatment agent such as a silane coupling agent, as necessary. Examples of the surface treatment agent include vinyltrimethoxysilane, vinyltriethoxysilane, vinyltrichlorosilane, vinyltris(β-methoxyethoxy)silane, γ-methacryloyloxypropyltrimethoxysilane, 11-methacryloyloxyundecyltrimethoxysilane, γ-glycidoxypropyltrimethoxysilane, γ-mercaptopropyltrimethoxysilane, and γ-aminopropyltriethoxysilane.

An organic-inorganic composite filler is obtained by previously adding a monomer compound to the above-mentioned inorganic filler to obtain a paste, followed by polymerization and pulverization. As the organic-inorganic composite filler, for example, a TMPT filler (obtained by mixing trimethylolpropane methacrylate and silica filler and polymerizing the resulting mixture, followed by pulverization) can be used. The shape of the particles of the organic-inorganic composite filler is not particularly limited, and the particle diameter of the filler can be selected as appropriate for use. In terms of the handling properties of the obtained curable composition and the mechanical strength of the cured product of the curable composition, the average particle diameter of the organic-inorganic composite filler is preferably 0.001 to 50 μm, and more preferably 0.001 to 10 μm.

In order to impart fluorine sustained releasability to the curable composition (A), it is preferable to use, as the filler (a4), at least one selected from the group consisting of fluoroaluminosilicate glass, calcium fluoroaluminosilicate glass, strontium fluoroaluminosilicate glass, barium fluoroaluminosilicate glass, and strontium calcium fluoroaluminosilicate glass. It is more preferable to use fluoroaluminosilicate glass and/or barium fluoroaluminosilicate glass. On the other hand, in order to impart radiopacity to the curable composition (A), it is preferable to use, as the filler (a4), at least one selected from the group consisting of barium glass, strontium glass, barium boroaluminosilicate glass, strontium boroaluminosilicate glass, strontium fluoroaluminosilicate glass, and barium fluoroaluminosilicate glass. It is more preferable to use barium glass and/or barium fluoroaluminosilicate glass.

The content of the filler (a4) in the curable composition (A) is preferably 0.5 to 85 wt. %. When the content of the filler is less than 0.5 wt. %, the effects obtained by adding the filler, that is, the effects of adjusting the viscosity of the curable composition (A) and improving the mechanical strength of the cured product of the curable composition (A) may not be obtained. On the other hand, when the content of the filler is more than 85 wt. %, the curable composition (A) may become too viscous and more difficult to handle. As described later, the curable composition (A) of the present invention is used preferably for dental bonding materials, dental composite resins, dental cements, etc. When the curable composition (A) is used as a dental composite resin or a dental cement, in terms of the viscosity of the curable composition (A) and the mechanical strength of the cured product of the curable composition (A), the content of the filler (a4) in the curable composition (A) is preferably 45 to 85 wt. %, and more preferably 47 to 80 wt. %.

In the present invention, the curable composition (A) may contain an acid group-containing radical polymerizable monomer (a5) in order to improve the adhesive properties to tooth structures and prostheses.

The acidic group-containing radical polymerizable monomer (a5) used in the present invention is, for example, a polymerizable monomer having at least one acidic group such as a phosphate group, a pyrophosphate group, a thiophosphate group, a phosphonate group, a carboxylate group, or a sulfonate group, and also having at least one radical polymerizable group such as an acryloyl group, a methacryloyl group, a vinyl group, or a styrene group. In terms of radical polymerizability and safety, the acidic group-containing radical polymerizable monomer (a5) preferably has a (meth)acryloyl group. That is, the acidic group-containing radical polymerizable monomer (a5) is preferably a (meth)acrylate polymerizable monomer or a (meth)acrylamide polymerizable monomer. One type of the acidic group-containing radical polymerizable monomer (a5) may be used alone, or two or more types thereof may be used in appropriate combination. Specific examples of the acidic group-containing radical polymerizable monomer (a5) are listed below.

Examples of the phosphate group-containing radical polymerizable monomer include: 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, 2-methacryloyloxyethyl-(4-methoxyphenyl) hydrogen phosphate, and 2-methacryloyloxypropyl-(4-methoxyphenyl) hydrogen phosphate; and their acid chlorides, alkali metal salts, and amine salts.

Examples of the pyrophosphate group-containing radical polymerizable monomer include: bis[2-(meth)acryloyloxyethyl]pyrophosphate, bis[4-(meth)acryloyloxybutyl]pyrophosphate, bis[6-(meth)acryloyloxyhexyl]pyrophosphate, bis[8-(meth)acryloyloxyoctyl]pyrophosphate, and bis[10-(meth)acryloyloxydecyl]pyrophosphate; and their acid chlorides, alkali metal salts, and ammonium salts.

Examples of the thiophosphate group-containing radical polymerizable monomer include: 2-(meth)acryloyloxyethyl dihydrogen thiophosphate, 3-(meth)acryloyloxypropyl dihydrogen thiophosphate, 4-(meth)acryloyloxybutyl dihydrogen thiophosphate, 5-(meth)acryloyloxypentyl dihydrogen thiophosphate, 6-(meth)acryloyloxyhexyl dihydrogen thiophosphate, 7-(meth)acryloyloxyheptyl dihydrogen thiophosphate, 8-(meth)acryloyloxyoctyl dihydrogen thiophosphate, 9-(meth)acryloyloxynonyl dihydrogen thiophosphate, 10-(meth)acryloyloxydecyl dihydrogen thiophosphate, 11-(meth)acryloyloxyundecyl dihydrogen thiophosphate, 12-(meth)acryloyloxydodecyl dihydrogen thiophosphate, 16-(meth)acryloyloxyhexadecyl dihydrogen thiophosphate, and 20-(meth)acryloyloxyicosyl dihydrogen thiophosphate; and their acid chlorides, alkali metal salts and ammonium salts.

Examples of the phosphonate group-containing radical polymerizable monomer include: 2-(meth)acryloyloxyethylphenyl phosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexyl-3-phosphonoacetate, and 10-(meth)acryloyloxydecyl-3-phosphonoacetate; and their acid chlorides, alkali metal salts and ammonium salts.

Examples of the carboxylate group-containing radical polymerizable monomer include: monofunctional radical polymerizable monomers each having one carboxyl group or its acid anhydride group per molecule; and monofunctional radical polymerizable monomers each having two or more carboxyl groups or their acid anhydride groups per molecule.

Examples of the monofunctional radical polymerizable monomer having one carboxyl group or its acid anhydride group per molecule include: (meth)acrylic acid, N-(meth)acryloyl glycine, N-(meth)acryloyl aspartic acid, 2-(meth)acryloyloxyethyl hydrogen succinate, 2-(meth)acryloyloxyethyl hydrogen phthalate, 2-(meth)acryloyloxyethyl hydrogen malate, O-(meth)acryloyl tyrosine, N-(meth)acryloyl tyrosine, N-(meth)acryloylphenylalanine, N-(meth)acryloyl-p-aminobenzoic acid, N-(meth)acryloyl-o-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, and N-(meth)acryloyl-4-aminosalicylic acid; and compounds obtained by converting the carboxyl groups of the above compounds into acid anhydride groups.

Examples of the monofunctional radical polymerizable monomer having two or more carboxyl groups or their acid anhydride groups per molecule include 6-(meth)acryloyloxyhexane-1,1-dicarboxylic acid, 9-(meth)acryloyloxynonane-1,1-dicarboxylic acid, 10-(meth)acryloyloxydecane-1,1-dicarboxylic acid, 11-(meth)acryloyloxyundecane-1,1-dicarboxylic acid, 12-(meth)acryloyloxydodecane-1,1-dicarboxylic acid, 13-(meth)acryloyloxytridecane-1,1-dicarboxylic acid, 4-(meth)acryloyloxyethyl trimellitate, 4-(meth)acryloyloxyethyl trimellitate anhydride, 4-(meth)acryloyloxybutyl trimellitate, 4-(meth)acryloyloxyhexyl trimellitate, 4-(meth)acryloyloxydecyl trimellitate, 2-(meth)acryloyloxyethyl-3'-(meth)acryloyloxy-2'-(3,4-dicarboxybenzoyloxy)propyl succinate, 6-(meth)acryloyloxyethylnaphthalene-1,2,6-tricarboxylic acid anhydride, 6-(meth)acryloyloxyethylnaphthalene-2,3,6-tricarboxylic acid anhydride, 4-(meth)acryloyloxyethylcarbonylpropionoyl-1,8-naphthalic acid anhydride, and 4-(meth)acryloyloxyethylnaphthalene-1,8-tricarboxylic acid anhydride.

Examples of the sulfonate group-containing radical polymerizable monomer include 2-(meth)acrylamide-2-methylpropanesulfonic acid, styrenesulfonic acid, and 2-sulfoethyl(meth)acrylate.

Among the above-mentioned examples of the acidic group-containing radical polymerizable monomer (a5), 10-(meth)acryloyloxydecyl dihydrogen phosphate, 4-(meth)acryloyloxyethyl trimellitate anhydride, 4-(meth)acryloyloxyethyl trimellitate, 11-(meth)acryloyloxyundecane-1,1-dicarboxylic acid, and 2-(meth)acrylamide-2-methylpropanesulfonic acid are preferred in terms of adhesive properties.

When the content of the acidic group-containing radical polymerizable monomer (a5) is too low, the effects of addition of the acidic group-containing radical polymerizable monomer (a5) may not be obtained. When the content of the acidic group-containing radical polymerizable monomer (a5) is too high, the radical polymerizable monomers in the curable composition (A) are more likely to be polymerized, which may cause a decrease in the storage stability of the curable composition (A). Therefore, the content of the acidic group-containing radical polymerizable monomer (a5) is preferably 1 to 40 parts by weight, more preferably 3 to 30 parts by weight, and even more preferably 5 to 20 parts by weight, in 100 parts by weight of the radical polymerizable monomers contained in the curable composition (A).

In the present invention, the curable composition (A) may contain a vanadium compound (a6) and/or a copper compound (a7) as a polymerization accelerator for redox polymerization. When the curable composition (A) contains the vanadium compound (a6) and/or the copper compound (a7), the mechanical strength and elastic modulus of the cured product of the curable composition are increased and thus the water resistance thereof is increased.

Preferably, the vanadium compound (a6) is a compound which is soluble in radical polymerizable monomers. Specific examples of such a vanadium compound include vanadium acetylacetonate, vanadyl acetylacetonate, vanadyl stearate, vanadium naphthenate, vanadium benzoyl acetonate, vanadyl oxalate, bis(maltolato)oxovanadium (IV), oxobis(1-phenyl-1,3-butanedionate)vanadium (IV), vanadium (V) oxytriisopropoxide, ammon metavanadate (V), sodium metavanadate (V), vanadium pentoxide (V), divanadium tetraoxide (IV), and vanadyl sulfate (IV). Among them, in terms of adhesive properties, etc., vanadium acetylacetonate, vanadyl acetylacetonate, and bis(maltolato)oxovanadium (IV) are preferred, and vanadyl acetylacetonate and bis(maltolato)oxovanadium (IV) are more preferred. One type of the vanadium compound (a6) can be used alone, or two or more types thereof can be used in combination.

When the content of the vanadium compound (a6) is too low, the effects of addition of the vanadium compound (a6) may not be obtained. When the content of the vanadium compound (a6) is too high, the radical polymerizable monomers in the curable composition (A) are more likely to be polymerized, which may cause a decrease in the storage stability of the curable composition (A). Therefore, the content of the vanadium compound (a6) is preferably 0.005 to 0.30 parts by weight, more preferably 0.008 to 0.15 parts by weight, and even more preferably 0.01 to 0.10 parts by weight, with respect to 100 parts by weight of the radical polymerizable monomers contained in the curable composition (A).

Preferably, the copper compound (a7) is a compound which is soluble in radical polymerizable monomers. Specific examples of such a copper compound include: copper carboxylates such as copper acetate, copper isobutyrate, copper gluconate, copper citrate, copper phthalate, copper tartrate, copper oleate, copper octylate, copper octanoate, copper naphthenate, copper methacrylate, and copper-4-cyclohexyl butyrate; copper β-diketones such as copper acetylacetonate, copper trifluoroacetylacetonate, copper hexafluoroacetylacetonate, copper 2,2,6,6-tetramethyl-3,5-heptanedionate, and copper benzoylacetonate; copper β-ketoesters such as copper ethylacetoacetate; copper alkoxides such as copper methoxide, copper ethoxide, copper isopropoxide, copper 2-(2-butoxyethoxy)ethoxide, and copper 2-(2-methoxyethoxy)ethoxide; copper dithiocarbamates such as dimethyldithiocarbamate; salts of copper and inorganic acids such as copper nitrate; and copper chloride. These can be used alone, or two or more of them can be used in combination. Among these, in terms of solubility in and reactivity with the radical polymerizable monomers, copper carboxylate, copper β-diketone, and copper β-ketoester are preferred, and copper acetate and copper acetylacetonate are particularly preferred.

When the content of the copper compound (a7) is too low, the effects of addition of the copper compound (a7) may not be obtained. When the content of the copper compound (a7) is too high, the radical polymerizable monomers in the curable composition (A) are more likely to be polymerized, which may cause a decrease in the storage stability of the curable composition (A). Therefore, the content of the copper compound (a7) is preferably 0.0001 to 0.01 parts by weight, more preferably 0.0002 to 0.005 parts by weight, and even more preferably 0.0003 to 0.003 parts by weight, with respect to 100 parts by weight of the radical polymerizable monomers contained in the curable composition (A).

The curable composition (A) may further contain a photopolymerization initiator to prepare the curable composition (A) as a dual-cure material. Examples of the photopolymerization initiator includes (bis)acylphosphine oxides, thioxanthones or quaternary ammonium salts of thioxanthones, ketals, α-diketones, coumarins, anthraquinones, benzoin alkyl ether compounds, and α-amino ketone compounds. The curable composition (A) may further contain a chemical polymerization initiator in addition to the above-mentioned polymerization initiators (a2) and (a3).

The curable composition (A) may further contain a photopolymerization initiator and a polymerization accelerator for a chemical polymerization initiator in addition to the above-mentioned polymerization initiators (a2) and (a3). Examples of the polymerization accelerator include amines, sulfinic acid and salts thereof, borate compounds, barbituric acid derivatives, triazine compounds, tin compounds, halogen compounds, aldehydes, thiol compounds, sulfite, and bisulfite.

In addition, the curable composition (A) may further contain a pH adjusting agent, a polymerization inhibitor, an ultraviolet ray absorber, a thickener, a colorant, an antibacterial agent, a flavor, etc. as long as they do not impair the effects of the present invention.

In the present invention, in terms of storage stability, the curable composition (A) is preferably prepared as a two-part composition including separate two parts: the hydroperoxide compound (a2); and the cyclic thiourea compound (a3). When the part containing the hydroperoxide compound (a2) is referred to as a part A and the part containing the cyclic thiourea compound (a3) is referred to as a part B, it is preferable to add the radical polymerizable monomer (a1) having no acidic group to the part A and the part B respectively. In the case where the curable composition (A) contains the filler (a4), the filler (a4) may be added to either the part A or the part B, or may be added to both of the part A and the part B. In the case where the curable composition (A) contains the acid group-containing radical polymerizable monomer (a5), it is preferable that only the part A contain the acidic group-containing radical polymerizable monomer (a5). Furthermore, in the case where the curable composition (A) contains the vanadium compound (a6) or the copper compound (a7), it is preferable that only the part B contain the vanadium compound (a6) or the copper compound (a7). When the part B of the curable composition (A) contains the vanadium compound (a6), the content of the vanadium compound (a6) is preferably 0.003 to 0.15 wt. %, and more preferably 0.005 to 0.1 wt. %, with respect to the total weight of the part B components. When the part B of the curable composition (A) contains the copper compound (a7), the content of the copper compound (a7) is preferably 0.00005 to 0.02 wt. %, and more preferably 0.0001 to 0.002 wt. %, with respect to the total weight of the part B components.

The curable composition (A) of the present invention containing a radical polymerizable monomer, and a hydroperoxide compound and a specific cyclic thiourea compound as a redox polymerization initiator has high adhesive properties, in particular high adhesive properties to tooth structures. In addition, the curable composition (A) of the present invention has moderate curability, and when the curable composition (A) is a two-part composition, it has a sufficiently high cure rate while providing a sufficient working time after the two parts are mixed to prepare the curable composition (A). In particular, it is possible to achieve both high adhesive properties and moderate curability under a wider range of reaction conditions (such as a catalyst and the presence of acid) and it is easier to adjust the curing time and working time of the composition than the case where a conventional thiourea compound is used. Furthermore, the curability of the curable composition (A) of the present invention is maintained almost unchanged even after long-term storage at room temperature or higher, which means that the curable composition (A) has excellent storage stability. In addition, the cured product of the curable composition (A) of the present invention has high transparency. Therefore, the curable composition (A) of the present invention is suitable for use in dental applications. When the curable composition (A) is used for dental applications, it is preferable to prepare the curable composition (A) as a dental bonding material, a dental composite resin, a dental cement, or the like, and it is more preferable to prepare the curable composition (A) as a dental cement. In this case, the curable composition (A) exhibits moderately high adhesive properties even in the presence of acid. Therefore, it is also possible to prepare the curable composition (A) containing the radical polymerizable monomer (a1) having no acidic group, as a self-adhesive dental material that requires no pretreatment agent such as a primer.

In order to further improve the adhesive properties, the present invention may be configured as an adhesive kit containing: a pretreatment agent (B) containing an acidic group-containing radical polymerizable monomer (b1), a polymerization accelerator (b2), a solvent (b3), and a hydrophilic radical polymerizable monomer (b4) having no acidic group; and the curable composition (A).

In the present invention, the acidic group-containing radical polymerizable monomer (b1) is the same as the acidic group-containing radical polymerizable monomer (a5) contained in the curable composition (A). In terms of adhesive properties, 10-(meth)acryloyloxydecyl dihydrogen phosphate, 4-(meth)acryloyloxyethyl trimellitate anhydride, 4-(meth)acryloyloxyethyl trimellitate, 11-(meth)acryloyloxyundecane-1,1-dicarboxylic acid, and 2-(meth)acrylamide-2-methylpropane sulfonic acid are preferred.

The content of the acidic group-containing radical polymerizable monomer (b1) in the pretreatment agent (B) is preferably 3 to 35 wt. %, more preferably 5 to 30 wt. %, and even more preferably 10 to 25 wt. %. When the content of the above polymerizable monomer (b1) is 3 wt. % or more, demineralization of tooth structures by the pretreatment agent (B) is further promoted, which contributes to improving the adhesiveness to the tooth structures. On the other hand, when the content of the polymerizable monomer (b1) is 35 wt. % or less, it is easier to obtain a more homogeneous solution as the pretreatment agent (A), which leads to improvement of the handling properties and adhesive properties to tooth structures.

Examples of the polymerization accelerator (b2) used in the present invention include amines, sulfinic acids and salts thereof, borate compounds, barbituric acid derivatives, triazine compounds, vanadium compounds, copper compounds, tin compounds, halogen compounds, aldehydes, thiol compounds, sulfite, bisulfite, and thiourea compounds. A vanadium compound (b2-1) and/or a copper compound (b2-2) are preferred.

As the vanadium compound (b2-1) and/or the copper compound (b2-2), the same compounds as the vanadium compound (a6) or the copper compound (a7) contained in the curable composition (A) can be used.

When the content of the vanadium compound (b2-1) in the pretreatment agent (B) is too low, the adhesive properties to tooth structures tend to decrease. When the content of the vanadium compound (b2-1) is too high, the working time tends to decrease. Therefore, the content of the vanadium compound (b2-1) in the pretreatment agent (B) is preferably 0.1 to 1 wt. %, more preferably 0.2 to 0.7 wt. %, and even more preferably 0.3 to 0.6 wt. %.

When the content of the copper compound (b2-2) in the pretreatment agent (B) is too low, the adhesive properties to tooth structures tend to decrease. When the content of the copper compound (b2-2) is too high, the working time tends to decrease. Therefore, the content of the copper compound (b2-2) in the pretreatment agent (B) is preferably 0.02 to 0.2 wt. %, and more preferably 0.04 to 0.15 wt. %.

The solvent (b3) used in the present invention not only increases the mutual solubility of the components of the pretreatment agent but also increases the penetration of the components of the pretreatment agent into tooth structures. As the solvent (b3), water or a water-soluble organic solvent can be suitably used. As the water-soluble organic solvent, an organic solvent having a boiling point of 150° C. or less under normal pressure and having a water solubility of 5 wt. % or more, and more preferably 30 wt. % or more at 25° C. is usually used. An organic solvent having a boiling point of 150° C. or less under normal pressure and having a desired water solubility is used most preferably. In particular, the water-soluble organic solvent having a boiling point of 100° C. or less under normal pressure is preferred. Specific examples of such an organic solvent include ethanol, methanol, 1-propanol, isopropyl alcohol, acetone, methyl ethyl ketone, 1,2-dimethoxyethane, 1,2-diethoxyethane, and tetrahydrofuran. One type of the solvent (b3) can be used alone, or two or more types thereof can be used in combination. When the solvent (b3) contains water, excessive evaporation of the solvent can be prevented and the adhesive properties to dentin can be improved. Therefore, the solvent (b3) preferably contains water. The water content in the solvent (b3) is preferably 60 wt. % or more, more preferably 80 wt. % or more, and even more preferably 90 wt. % or more, and most preferably 100 wt. %.

The content of the solvent (b3) in the pretreatment agent (B) is preferably 10 to 60 wt. %, more preferably 25 to 50 wt. %, and even more preferably 30 to 45 wt. %. When the content of the solvent (b3) is 10 wt. %, the pretreatment agent (B) has more appropriate demineralization effect on tooth structures and contributes to improving the adhesive properties to the tooth structures. When the content of the solvent (b3) is 60 wt. % or less, the solvent (b3) is easier to evaporate after the pretreatment agent (B) is applied to an adherend, and variations in the application depending on the operator's skill are reduced, which is advantageous for obtaining more stable adhesive properties.

The hydrophilic radical polymerizable monomer (b4) having no acidic group used in the present invention penetrates into tooth structures, increases the degree of polymerization of the resulting cured product, and improves its adhesive properties.

In this description, the hydrophilic radical polymerizable monomer (b4) having no acidic group refers to a hydrophilic radical polymerizable monomer having no acidic group and having a water solubility of 5 wt. % or more at 25° C. The water solubility of the hydrophilic radical polymerizable monomer (b4) is more preferably 10 wt. % or more, and even more preferably 30 wt. % or more.

The hydrophilic radical polymerizable monomer (b4) having no acidic group is, for example, a hydrophilic radical polymerizable monomer having the above-mentioned water solubility, having no acidic group (such as a phosphate group, a pyrophosphate group, a thiophosphate group, a phosphonate group, a carboxylate group, and a sulfonate group), and having at least one radical polymerizable group (such as an acryloyl group, a methacryloyl group, a vinyl group, and a styrene group). In terms of radical polymerizability and safety, the hydrophilic radical polymerizable monomer (b4) having no acidic group preferably has a (meth)acryloyl group.

The hydrophilic radical polymerizable monomer (b4) having no acidic group may be monofunctional (b4-1), difunctional (b4-2), or tri- or higher-functional (b4-3).

Specific examples of the monofunctional hydrophilic radical polymerizable monomer (b4-1) having no acidic group include 2-hydroxyethyl(meth)acrylate, 2-hydroxypropyl(meth)acrylate, 3-hydroxypropyl(meth)acrylate, 1,3-dihydroxypropyl(meth)acrylate, 2,3-dihydroxypropyl(meth) acrylate, 2-hydroxybutyl(meth)acrylate, propylene glycol mono(meth)acrylate, glycerol mono(meth)acrylate, erythritol mono(meth)acrylate, N-methylol(meth)acrylamide, N-hydroxyethyl(meth)acrylamide, N,N-(dihydroxyethyl) (meth)acrylamide, methoxypolyethylene glycol(meth)acrylate, (meth)acryloyl morpholine, and diethyl(meth)acrylamide. Among these, in terms of improving the penetrability into a collagen layer of dentin, 2-hydroxyethyl(meth)acrylate, 3-hydroxypropyl(meth)acrylate, glycerol mono(meth) acrylate, erythritol mono(meth)acrylate, methoxypolyethylene glycol(meth)acrylate, (meth)acryloyl morpholine, and diethyl(meth)acrylamide are preferred, and 2-hydroxyethyl (meth)acrylate is particularly preferred.

Examples of the difunctional hydrophilic radical polymerizable monomer (b4-2) having no acidic group include erythritol di(meth)acrylate, sorbitol di(meth)acrylate, mannitol di(meth)acrylate, pentaerythritol di(meth)acrylate, dipentaerythritol di(meth)acrylate, glycerol di(meth)acrylate, 1,2-bis(3-methacryloyloxy-2-hydroxypropyloxy)ethane, ethylenebis(meth)acrylamide, propylenebis(meth)acrylamide, butylenebis(meth)acrylamide, N,N'-(dimethyl) ethylene-bis(meth)acrylamide, N,N'-diethyl-1,3-propylenebis(meth)acrylamide, bis[2-(2-methyl-(meth)acrylamino) ethoxycarbonyl]hexamethylenediamine, and 2,2,4-trimethylhexamethylene-1,6-bis(meth)acrylamide. Among these, in terms of balance between penetrability into tooth structures and crosslinkability, glycerol di(meth)acrylate, 1,2-bis(3-methacryloyloxy-2-hydroxypropyloxy)ethane, propylenebis(meth)acrylamide, N,N'-(dimethyl)ethylene-bis(meth)acrylamide, and N,N'-diethyl-1,3-propylene-bis (meth)acrylamide are preferred, and 1,2-bis(3-methacryloyloxy-2-hydroxypropyloxy)ethane is more preferred.

Examples of tri- or higher-functional hydrophilic radical polymerizable monomer (b4-3) having no acidic group include pentaerythritol tri(meth)acrylate, pentaerythritol tetra(meth)acrylate, dipentaerythritol tri(meth)acrylate, dipentaerythritol tetra(meth)acrylate, and dipentaerythritol penta(meth)acrylate. Among these, in terms of balance between penetrability into tooth structures and crosslinkability, dipentaerythritol tetra(meth)acrylate and dipentaerythritol penta(meth)acrylate are more preferred.

The content of the hydrophilic radical polymerizable monomer (b4) having no acidic group in the pretreatment agent (B) is preferably 35 to 85 wt. %, more preferably 37 to 75 wt. %, and even more preferably 40 to 65 wt. %. When the content of the polymerizable monomer (b4) is 35 wt. % or more, the effect of addition of the polymerizable monomer (b4), that is, improvement of adhesive properties, can be seen more clearly. On the other hand, when the content of the polymerizable monomer (b4) is 85 wt. % or less, the pretreatment (B) can exhibit the effect of demineralizing tooth structures at a high level without impairing the effect of the addition of the polymerizable monomer (b4).

In a preferred embodiment, the hydrophilic radical polymerizable monomer (b4) having no acidic group contains a difunctional hydrophilic radical polymerizable monomer (b4-2) having no acidic group. In this case, adhesive properties to tooth structures, particularly adhesive properties to dentin are further enhanced. In a more preferred embodiment, the hydrophilic radical polymerizable monomer (b4) having no acidic group contains both a difunctional hydrophilic radical polymerizable monomer (b4-2) and a monofunctional hydrophilic radical polymerizable monomer (b4-1). When the pretreatment (B) contains both of the polymerizable monomers (b4-1) and (b4-2), its penetration into tooth structures is further increased and thus its adhesive properties are further improved.

The content of the difunctional hydrophilic radical polymerizable monomer (b4-2) having no acidic group is preferably 1 to 20 parts by weight, more preferably 2 to 15 parts by weight, and even more preferably 5 to 12 parts by weight, in 100 parts by weight of the total amount of the radical polymerizable monomers contained in the pretreatment agent (B). In addition, as described above, it is preferable that the hydrophilic radical polymerizable monomer (b4) having no acidic group contain both the difunctional hydrophilic radical polymerizable monomer (b4-2) and the monofunctional hydrophilic radical polymerizable monomer (b4-1). In this case, the content of the difunctional hydrophilic radical polymerizable monomer (b4-2) is preferably 1 to 35 parts by weight, more preferably 2 to 15 parts by weight, and even more preferably 5 to 12 parts by weight, in 100 parts by weight of the total amount of the radical polymerizable monomers contained in the pretreatment agent (B). In addition, the content of the monofunctional hydrophilic radical polymerizable monomer (b4-1) is preferably 20 to 85 parts by weight, more preferably 40 to 72 parts by weight, and even more preferably 45 to 69 parts by weight, in 100 parts by weight of the total amount of the radical polymerizable monomers contained in the pretreatment agent (B).

In terms of its storage stability, the pretreatment agent (B) may further contain a polymerization inhibitor (b5). Examples of the polymerization inhibitor include 3,5-di-t-butyl-4-hydroxytoluene, hydroquinone, dibutylhydroquinone, dibutylhydroquinone monomethyl ether, 2,6-t-butylphenol, and 4-methoxyphenol. One of these may be added, or two or more of these may be added. The content of the polymerization inhibitor in the pretreatment agent (B) is preferably 0.2 to 5 wt. %, more preferably 0.4 to 5 wt. %, even more preferably 0.7 to 3 wt. %, and still more preferably 1 to 2 wt. %. When the content of the polymerization inhibitor (b5) in the pretreatment agent (B) is less than 0.4 wt. %, the storage stability of the pretreatment agent is not sufficient, which may cause discoloration of the pretreatment agent. When the content of the polymerization inhibitor (b5) is more than 5 wt. %, the polymerization inhibitor does not dissolve in the pretreatment agent composition, and may be precipitated during storage thereof or during preparation of the composition.

The pretreatment agent (B) may further contain a filler. For example, the same filler as the above-mentioned filler (a4) contained in the curable composition (A) can be used.

In addition, the pretreatment agent (B) may further contain a pH adjusting agent, an ultraviolet ray absorber, a thickener, a colorant, an antibacterial agent, a flavor, etc.

In the present invention, the packaging of the pretreatment agent (B) may be determined as appropriate in terms of storage stability and is not particularly limited. For example, in the case where a component that serves in itself as a polymerization catalyst, like sulfinic acid and a salt thereof, is contained, this polymerization catalyst may be divided into portions, which can be mixed together just before use. However, it is preferable that the pretreatment agent (B) be in the form of a single package liquid in terms of ease of handling.

The adhesive kit of the present invention has excellent adhesive properties, in particular adhesive properties to tooth structures, and moderate curability, and provides sufficient working time after the pretreatment agent comes into contact with an adhesive. The adhesive kit also has excellent storage stability. In addition, the cured product of the curable composition (A) has high transparency. Therefore, it is suitable for use in dental applications. When the adhesive kit of the present invention is used in dental applications, the kit can include the pretreatment agent (B) as a dental primer and the curable composition (A) as a dental bonding material, a dental composite resin, a dental cement, or the like. In particular, a preferred form of the adhesive kit is a dental cement kit including the pretreatment agent (B) as a dental primer and the curable composition (A) as a dental cement.

EXAMPLES

Hereinafter, the present invention is described in detail with reference to examples and comparative examples. The present invention is not limited to these Examples. Abbreviations used hereinafter are listed below.
[Polymerizable Monomer Having No Acidic Group]
  #801: 1,2-bis(3-methacryloyloxy-2-hydroxypropoxy)ethane
  HEMA: 2-hydroxyethyl methacrylate
  BisGMA: 2,2-bis[4-(3-methacryloyloxy)-2-hydroxypropoxyphenyl]propane
  D2.6E: 2,2-bis(4-methacryloyloxypolyethoxyphenyl)propane (average number of moles of added ethoxy groups: 2.6)
  3G: triethylene glycol dimethacrylate
[Acidic Group-Containing Polymerizable Monomer]
  MDP: 10-methacryloyloxydecyl dihydrogen phosphate
[Hydroperoxide Compound]
  THP: 1,1,3,3-tetramethylbutyl hydroperoxide
[Thiourea Derivative]
  DMETU: 4,4-dimethyl-2-imidazolidinethione
  METU: 4-methyl-2-imidazolidinethione
  DEETU: 4,4-diethyl-2-imidazolidinethione
  DMPTU: 5,5-dimethyl-3,4,5,6-tetrahydropyrimidine-2(1H)-thione
  CPPTU: 5-(2-chlorophenyl)-3,4,5,6-tetrahydropyrimidine-2(1H)-thione
  EtTU: 2-imidazolidinethione
  PrTU: tetrahydro-2(1H)pyrimidinethione
  BzTU: N-benzoylthiourea
  TMTU: N,N,N'-trimethylthiourea
[Vanadium Compound]
  VOAA: vanadyl acetylacetonate
  BMOV: bis(maltolato)oxovanadium (IV)
[Copper Compound]
  CuAA2: copper (II) acetylacetonate
  Cu(OAc)2: copper (II) acetate
[Polymerization Inhibitor]
  BHT 3,5-di-t-butyl-4-hydroxytoluene
[Ultraviolet Absorber]
  TN326: TINUVIN 326 (manufactured by Chiba Specialty Chemicals, Inc.)
[Photopolymerization Initiator]
  CQ: camphorquinone
[Filler]
  8235: silane-treated barium glass powder manufactured by Schott AG, average particle diameter: 2 μm, silane treatment concentration: 1.4%
  G018-117: silane-treated barium fluoroaluminosilicate glass powder manufactured by Schott AG, average particle diameter: 2 μm, silane treatment concentration: 1.4%
  Ar380: silica fine particles "AEROSIL (registered trademark) 380" manufactured by Nippon Aerosil Co., Ltd., average particle diameter: 7 nm
[Others]
  DMAEMA: dimethylaminoethyl methacrylate
  JJA: 4-(N,N-dimethylamino)benzoic acid ethyl Examples 1 to 17 and Comparative Examples 1 to 5

The curable compositions (A) and the pretreatment agents (B) of Examples 1 to 17 and Comparative Examples 1 to 5 were each prepared in the following manner and their characteristics were evaluated. Tables 2 to 4 show the results.
[Preparation of Curable Composition (A)]
Monomer components shown in Tables 2 to 4 were mixed at weight ratios shown in Tables 2 to 4 at ordinary temperature to prepare monomer compositions. Then, the monomer compositions and various fillers were mixed at weight ratios shown in Tables 2 to 4 at ordinary temperature to prepare pastes A and pastes B. Next, 15 g of each paste B was put into a resin container of "CLEARFIL (registered trademark) FII" (manufactured by Kuraray Noritake Dental Inc.) and covered the container. The container was allowed to stand in a thermostat set at 60° C. for 24 hours and then cooled to ordinary temperature for use. The paste A and the paste B obtained as described above were loaded into a paste container as an automix syringe of "CLEARFIL (registered trademark) Esthetic Cement" (manufactured by Kuraray Noritake Dental Inc.). When the paste A and the paste B were mixed to obtain a composition, a mixing tip ("CLEARFIL (registered trademark) Esthetic Cement, Mixing Tip, manufactured by Kuraray Noritake Dental Inc.) was attached to the tip of the paste container, and the paste A and the paste B were mixed in equal amounts (at a volume ratio of 1:1) using this mixing tip so as to obtain the composition.
[Preparation of Pretreatment Agent (B)]
Components shown in Tables 2 to 4 were mixed at weight ratios shown in Tables 2 to 4 at ordinary temperature to prepare primer compositions as the pretreatment agents (B). Each pretreatment agent (B) obtained was loaded into a container of "CLEARFIL (registered trademark) Mega Bond (registered trademark) Primer" (manufactured by Kuraray Noritake Dental Inc.) for use.
[Method for Evaluating Solubility of Thiourea Compound in Radical Polymerizable Monomer]
2.97 g of triethylene glycol dimethacrylate was added to 0.030 g of a thiourea compound, and 2.85 g of triethylene glycol dimethacrylate was added to 0.15 g of the thiourea compound, respectively. Then, the resulting mixtures were each stirred at 25° C. for 1 hour and visually observed, and their solubility was evaluated according to the following criteria.

TABLE 1

| Ratings | Criteria |
| --- | --- |
| A | Solubility in 3 G is 5.0 wt. % or more at 25° C. |
| B | Solubility in 3 G is 1.0 wt. % or more and less than 5.0 wt. % at 25° C. |
| C | Solubility in 3 G is less than 1.0 wt. % at 25° C. |

[Method for Evaluating Adhesive Properties to Bovine Enamel and Bovine Dentin]
The labial surface of bovine mandibular anterior teeth was polished with silicon carbide paper (#80) (manufactured by Nihon Kenshi Co., Ltd.) under running water to obtain a sample with an exposed flat enamel surface and a sample with an exposed flat dentin surface. The samples thus obtained were each further polished with #1000 silicon carbide paper (manufactured by Nihon Kenshi Co., Ltd.) under running water. After polishing, water on the surface of each sample was air-blown to dry. An about 150 μm-thick adhesive tape having a circular hole with a diameter of 3 mm was attached to the dry smooth surface of the sample to define the bonding area.

A composition was obtained by mixing the paste A and the paste B of the curable composition (A) at a volume ratio of 1:1 using a mixing tip as described above and kneading the mixture, and the composition was placed on each bovine tooth obtained. The tooth with the composition placed thereon was covered with a release film ("EVAL" (trade name) manufactured by Kuraray Co., Ltd.), and then allowed to stand at ordinary temperature for 1 hour to be cured. Next, using a dental resin cement ("PANAVIA 21" (trade name) manufactured by Kuraray Noritake Dental Inc.), a stainless steel cylindrical rod (with a diameter of 7 mm and a length of 2.5 cm) was bonded at its one end face (with a circular cross section) to the surface of the obtained cured product and allowed to stand for 30 minutes. Thereafter, the excess cement composition around the stainless steel cylindrical rod was removed and then the test sample was immersed in distilled water. The test sample having been immersed in distilled water was allowed to stand in a thermostat set at 37° C. for 24 hours. Thus, a specimen was obtained. A total of 5 such specimens were prepared for the bond strength test.

In the case of an adhesive kit, the pretreatment agent (B) prepared as described above was applied within the above-mentioned circular hole using a brush and left for 20 seconds. Then, the surface was air-blown to dry the applied pretreatment agent (B) until the pretreatment agent (B) lost its flowability. A composition was obtained by mixing the paste A and the paste B of the curable composition (A) at a volume ratio of 1:1 using a mixing tip as described above and kneading the mixture, and the composition was placed on the surface coated with the pretreatment agent (B). The sample with the composition placed thereon was covered with a release film ("EVAL" (trade name) manufactured by Kuraray Co., Ltd.), and then allowed to stand at ordinary temperature for 1 hour to be cured. Next, using a dental resin cement ("PANAVIA 21" (trade name) manufactured by Kuraray Noritake Dental Inc.), a stainless steel cylindrical rod (with a diameter of 7 mm and a length of 2.5 cm) was bonded at its one end face (with a circular cross section) to the surface of the obtained cured product and allowed to stand for 30 minutes. Thereafter, the excess cement composition around the stainless steel cylindrical rod was removed and then the test sample was immersed in distilled water. The test sample having been immersed in distilled water was allowed to stand in a thermostat set at 37° C. for 24 hours. Thus, a specimen was obtained. A total of 5 such specimens were prepared for the bond strength test.

For the above 5 specimens for the bond strength test, the tensile bond strength was measured using a universal testing machine (manufactured by Shimadzu Corporation) at a crosshead speed of 2 mm/min. The average of the measured values was used as the tensile bond strength.

[Measurement of Working Time at 23° C. (Initial)]
The working time at 23° C. (initial) of the curable composition (A) was measured according to JIS T 6611:2009 "6.4 Working time", except that a composition obtained by mixing the paste A and the paste B of the curable composition (A) at a volume ratio of 1:1 using a mixing tip and kneading the mixture was allowed to stand in a resin container immediately after the kneading.

[Measurement of Working Time at 23° C. (after Storage at 50° C. For 2 Weeks)]
An automix syringe filled with the curable composition (A) was stored in a thermostat set at 50° C. for 2 weeks, and then the working time was measured in the same manner as for the "working time at 23° C. (initial)".

[Measurement of Working Time at 23° C. (after Storage at 50° C. For 4 Weeks)]
An automix syringe filled with the curable composition (A) was stored in a thermostat set at 50° C. for 4 weeks, and then the working time was measured in the same manner as for the "working time at 23° C. (initial)".

[Measurement of Curing Time at 37° C. (Initial)]
The curing time at 37° C. (initial) of the curable composition (A) was measured according to JIS T 6611:2009 "6.5 Curing time", except that a composition obtained by mixing the paste A and the paste B of the curable composition (A) at a volume ratio of 1:1 using a mixing tip and kneading the mixture was allowed to stand in a resin container immediately after the kneading.

[Measurement of Curing Time at 37° C. (after Storage at 50° C. For 2 Weeks)]
An automix syringe filled with the curable composition (A) was stored in a thermostat set at 50° C. for 2 weeks, and then the curing time was measured in the same manner as for the "curing time at 37° C. (initial)".

[Measurement of Curing Time at 37° C. (after Storage at 50° C. For 4 Weeks)]
An automix syringe filled with the curable composition (A) was stored in a thermostat set at 50° C. for 4 weeks, and then the curing time was measured in the same manner as for the "curing time at 37° C. (initial)".

[Measurement of Flexural Strength and Flexural Modulus of Cured Product of Paste]
A polyester film was laid over a glass slide and a stainless steel frame of 2 mm long, 25 mm wide, and 2 mm deep was placed on the film. Next, a composition was obtained by mixing the paste A and the paste B of the curable composition (A) at a volume ratio 1:1 using a mixing tip and kneading the mixture, and the composition was loaded into the frame. Another polyester film and another glass slide were placed on the frame so as to sandwich the composition in the frame between the two glass slides, and a pressure was applied to bond the surfaces of the composition to the polyester films. The two glass slides were clamped with a 25 mm-wide alligator clip to fix the sample. The sample fixed with the alligator clip was allowed to stand in a thermostat set at 37° C. for 1 hour to allow the composition to cure through polymerization. The sample was taken out of the thermostat and the polymerized cured product of the composition was removed from the frame. The polymerized cured product was immersed in distilled water at 37° C. for 24 hours for storage, and the resulting product was subjected to a bending test. The polymerized cured product was subjected to a three-point bending test with a span of 20 mm at a crosshead speed of 1 mm/min. using a universal testing machine so as to measure the flexural strength and flexural modulus. The average of the measured values of the 5 specimens was determined to be the flexural strength or the flexural modulus of that sample.

[Measurement of Transparency ($\Delta L^*$) of Cured Product of Paste]
A disk-shaped sample (with a diameter of about 2 cm and a thickness of 1 mm) was prepared using the curable composition (A) in the following manner. A glass cover was placed on a glass slide, and two plate-like stainless steel spacers with a thickness of 1 mm were placed on the glass cover at a distance of at least 2.5 cm from each other. A composition was obtained by mixing the paste A and the paste B of the curable composition (A) at a volume ratio 1:1 using a mixing tip and kneading the mixture, and the composition was formed into a hemispherical shape and placed between the two spacers. Another glass cover and another glass slide were placed on the composition. The composition sandwiched between the two glass slides was pressed into a disk shape, and the resulting disk-shaped composition was allowed to stand in a thermostat set at 37° C. for 1 hour. Thus, the composition was completely cured. The thickness of the sample was limited within a range of 0.99 to 1.00 mm (a maximum thickness of 1.00 mm and a minimum thickness of 0.99 mm) because the test result significantly varies depending on the thickness of the sample.

The lightness (Lw*) of a specimen placed in front of a standard white plate and the lightness (Lb*) of the specimen placed in front of a standard black plate were measured using a spectrophotometer ("SE 6000" (trade name) manufactured by Nippon Denshoku Industries Co., Ltd.) that met the requirements of JIS Z 8729 under the conditions of a D65 illuminant and a 2° observer. The difference (ΔL*=(Lw*)−(Lb*)) between the lightness (Lw*) and the lightness (Lb*) was determined to be the transparency (ΔL*) of the cured product of the paste.

[In-Water Discoloration Test of Cured Product of Paste]

The thus-obtained disk-shaped sample (with a diameter of about 2 cm and a thickness of 1 mm) of the cured product of the paste composed of the curable composition (A) was placed in front of a standard white plate and the chromaticity coordinates of the sample in the L*a*b* color space were measured using a spectrophotometer ("SE 6000" (trade name) manufactured by Nippon Denshoku Industries Co., Ltd.) that met the requirements of JIS Z 8729 under the conditions of a D65 illuminant and a 2° observer, and the coordinates obtained were defined as L*0, a*0, and b*0. Next, the sample was placed in a screw-cap tube, which was then filled with distilled water and tightly capped, and allowed to stand in a thermostat set at 70° C. for 4 weeks. Thereafter, the chromaticity coordinates of the sample in the L*a*b* color space were measured in the same manner, and the coordinates obtained were defined as L*1, a*1, and b*1. The obtained values were respectively substituted into the following formula to obtain the value ΔE* as a measure of discoloration:

$$\Delta E^* = \{(L^*1-L^*0)^2 + (a^*1-a^*0)^2 + (b^*1-b^*0)^2\}^{1/2}$$

[Measurement of Working Time in Contact with Primer]

The labial surface of bovine mandibular anterior tooth was polished with silicon carbide paper (#80) (manufactured by Nihon Kenshi Co., Ltd.) under running water to obtain a sample with an exposed flat dentin surface. The area of the flat surface was large enough for the bottom of a cylinder with a diameter of 9 mm. The flat surface thus obtained was further polished with #1000 silicon carbide paper (manufactured by Nihon Kenshi Co., Ltd.), and then the sample was immersed in distilled water. Next, the circular cross section of a cylindrical SUS tip (with a diameter of 9 mm and a height of about 7 mm) was polished with #1000 silicon carbide paper (manufactured by Nihon Kenshi Co., Ltd.). The bovine tooth immersed in distilled water and the polished SUS tip thus obtained were allowed to stand in an open chamber set at 35° C. for 2 hours, and then used for the test.

After standing in the open chamber, water on the surface of the bovine tooth was air-blown to dry, and then was fixed on a glass slide with its smooth surface facing upward using utility wax (by GC Corporation). The glass slide on which the bovine tooth was fixed was placed on a working table in the open chamber, and the position of the bovine tooth was adjusted so that the working table and the smooth surface of the bovine tooth were parallel to each other. Next, the pretreatment agent (B) was applied to the above-mentioned smooth surface using a brush and left for 20 seconds. Then, the surface was air-blown to dry the applied pretreatment agent (B) until the pretreatment agent (B) lost its flowability.

Test Example 1

A composition was obtained by mixing the paste A and the paste B of the curable composition (A) at a volume ratio of 1:1 using a mixing tip as described above and kneading the mixture, and the composition was placed on the polished surface of the SUS tip. Then, the SUS tip was placed gently on the bovine tooth so that the surface of the tip on which the composition was placed was in contact with the smooth surface of the bovine tooth. Immediately after placing the SUS tip on the bovine tooth, a cylindrical weight (with a diameter of 3 cm) of 150 g was placed on the SUS tip for 1 second and then removed, at which time the measurement was started. 30 seconds after the start of the measurement, the SUS tip was touched gently with a finger to observe whether the SUS tip was moved or not, and then the observation was repeated every 10 seconds. The elapsed time to the time at which no movement of the SUS tip was observed was determined as the working time in contact with the primer.

TABLE 2

|  |  | Ex. 1 | Ex. 2 | Ex. 3 | Ex. 4 | Ex. 5 |
|---|---|---|---|---|---|---|
| Primer |  | P001 | P001 | P001 | P001 | P001 |
| MDP |  | 15.0 | 15.0 | 15.0 | 15.0 | 15.0 |
| #801 |  | 15.0 | 15.0 | 15.0 | 15.0 | 15.0 |
| HEMA |  | 35.0 | 35.0 | 35.0 | 35.0 | 35.0 |
| $H_2O$ |  | 32.0 | 32.0 | 32.0 | 32.0 | 32.0 |
| VOAA |  | 0.300 | 0.300 | 0.300 | 0.300 | 0.300 |
| BHT |  | 1.50 | 1.50 | 1.50 | 1.50 | 1.50 |
| DMAEMA |  | 2.70 | 2.70 | 2.70 | 2.70 | 2.70 |
| Paste A |  | A001 | A001 | A001 | A001 | A001 |
| Monomer | BisGMA | 36.0 | 36.0 | 36.0 | 36.0 | 36.0 |
| composition A | D2.6E | 37.0 | 37.0 | 37.0 | 37.0 | 37.0 |
|  | 3G | 17.0 | 17.0 | 17.0 | 17.0 | 17.0 |
|  | #801 | 10.0 | 10.0 | 10.0 | 10.0 | 10.0 |
|  | THP | 4.00 | 4.00 | 4.00 | 4.00 | 4.00 |
|  | JJA | 0.225 | 0.225 | 0.225 | 0.225 | 0.225 |

TABLE 2-continued

|  |  |  |  |  |  |  |
|---|---|---|---|---|---|---|
|  | TN326 | 0.225 | 0.225 | 0.225 | 0.225 | 0.225 |
|  | BHT | 0.0500 | 0.0500 | 0.0500 | 0.0500 | 0.0500 |
| Monomer composition A |  | 38.0 | 38.0 | 38.0 | 38.0 | 38.0 |
| 8235 |  | 51.0 | 51.0 | 51.0 | 51.0 | 51.0 |
| G018-117 |  | 10.0 | 10.0 | 10.0 | 10.0 | 10.0 |
| Ar380 |  | 1.00 | 1.00 | 1.00 | 1.00 | 1.00 |
| Paste B |  | B001 | B002 | B003 | B004 | B005 |
| Monomer | BisGMA | 15.0 | 15.0 | 15.0 | 15.0 | 15.0 |
| composition B | D2.6E | 70.0 | 70.0 | 70.0 | 70.0 | 70.0 |
|  | #801 | 15.0 | 15.0 | 15.0 | 15.0 | 15.0 |
|  | VOAA | 0.100 | 0.100 | 0.100 | 0.100 | 0.100 |
|  | BMOV | 0.000 | 0.000 | 0.000 | 0.000 | 0.000 |
|  | Cu(OAc)2 | 0.0000 | 0.0000 | 0.0000 | 0.0000 | 0.0000 |
|  | CuAA2 | 0.0000 | 0.0000 | 0.0000 | 0.0000 | 0.0000 |
|  | DMETU | 6.00 | 0.00 | 0.00 | 0.00 | 0.00 |
|  | METU | 0.00 | 6.00 | 0.00 | 0.00 | 0.00 |
|  | DEETU | 0.00 | 0.00 | 6.00 | 0.00 | 0.00 |
|  | DMPTU | 0.00 | 0.00 | 0.00 | 6.00 | 0.00 |
|  | CPPTU | 0.00 | 0.00 | 0.00 | 0.00 | 6.00 |
|  | CQ | 0.150 | 0.150 | 0.150 | 0.150 | 0.150 |
|  | BHT | 0.0500 | 0.0500 | 0.0500 | 0.0500 | 0.0500 |
| Monomer composition B |  | 42.0 | 38.0 | 38.0 | 38.0 | 38.0 |
| 8235 |  | 57.0 | 61.0 | 61.0 | 61.0 | 61.0 |
| Ar380 |  | 1.00 | 1.00 | 1.00 | 1.00 | 1.00 |
| Solubility of thiourea in polymerizable monomer |  | A | A | A | A | A |
| Adhesive properties to enamel (MPa) (initial) Tensile bond strength |  | 20.6 | 21.0 | 20.2 | 21.0 | 18.1 |
| Adhesive properties to dentin (MPa) (initial) Tensile bond strength |  | 19.2 | 19.1 | 18.2 | 18.7 | 15.2 |
| Working time at 23° C. (min.) (initial) |  | 5.0 | 5.8 | 4.8 | 5.0 | 6.2 |
| Working time at 23° C. (min.) (after storage at 50° C. for 2 weeks) |  | 5.2 | 6.0 | 5.0 | 5.5 | 5.9 |
| Working time at 23° C. (min.) (after storage at 50° C. for 4 weeks) |  | 5.3 | 5.9 | 5.2 | 5.7 | 6.0 |
| Curing time at 37° C. (min.) (initial) |  | 2.9 | 3.1 | 2.6 | 3.5 | 3.7 |
| Curing time at 37° C. (min.) (after storage at 50° C. for 2 weeks) |  | 3.0 | 3.2 | 2.8 | 3.2 | 3.5 |
| Curing time at 37° C. (min.) (after storage at 50° C. for 4 weeks) |  | 3.1 | 3.4 | 3.0 | 3.4 | 3.5 |
| Flexural strength of cured product of paste (MPa) |  | 132 | 129 | 130 | 129 | 128 |
| Flexural modulus of cured product of paste (GPa) |  | 6.7 | 6.1 | 6.5 | 5.8 | 5.9 |
| Transparency of cured product of paste (ΔL*) |  | 40.9 | 40.3 | 40.5 | 40.8 | 41.0 |
| In-water discoloration of cured product of paste (ΔE*) (after storage at 70° C. for 4 weeks) |  | 1.5 | 1.8 | 2.2 | 1.9 | 1.9 |
| Working time in contact with primer at 35° C. (sec.) |  | 50 | 60 | 60 | 60 | 60 |

|  |  | Ex. 6 | Ex. 7 | Ex. 8 | Ex. 9 |
|---|---|---|---|---|---|
| Primer |  | P001 | P001 | P001 | P001 |
| MDP |  | 15.0 | 15.0 | 15.0 | 15.0 |
| #801 |  | 15.0 | 15.0 | 15.0 | 15.0 |
| HEMA |  | 35.0 | 35.0 | 35.0 | 35.0 |
| H$_2$O |  | 32.0 | 32.0 | 32.0 | 32.0 |
| VOAA |  | 0.300 | 0.300 | 0.300 | 0.300 |
| BHT |  | 1.50 | 1.50 | 1.50 | 1.50 |
| DMAEMA |  | 2.70 | 2.70 | 2.70 | 2.70 |
| Paste A |  | A001 | A001 | A001 | A001 |
| Monomer | BisGMA | 36.0 | 36.0 | 36.0 | 36.0 |
| composition A | D2.6E | 37.0 | 37.0 | 37.0 | 37.0 |
|  | 3G | 17.0 | 17.0 | 17.0 | 17.0 |
|  | #801 | 10.0 | 10.0 | 10.0 | 10.0 |
|  | THP | 4.00 | 4.00 | 4.00 | 4.00 |
|  | JJA | 0.225 | 0.225 | 0.225 | 0.225 |
|  | TN326 | 0.225 | 0.225 | 0.225 | 0.225 |
|  | BHT | 0.0500 | 0.0500 | 0.0500 | 0.0500 |
| Monomer composition A |  | 38.0 | 38.0 | 38.0 | 38.0 |
| 8235 |  | 51.0 | 51.0 | 51.0 | 51.0 |
| G018-117 |  | 10.0 | 10.0 | 10.0 | 10.0 |
| Ar380 |  | 1.00 | 1.00 | 1.00 | 1.00 |
| Paste B |  | B006 | B007 | B008 | B009 |
| Monomer | BisGMA | 15.0 | 15.0 | 15.0 | 15.0 |
| composition B | D2.6E | 70.0 | 70.0 | 70.0 | 70.0 |
|  | #801 | 15.0 | 15.0 | 15.0 | 15.0 |
|  | VOAA | 0.000 | 0.000 | 0.000 | 0.000 |
|  | BMOV | 0.100 | 0.000 | 0.000 | 0.000 |
|  | Cu(OAc)2 | 0.0000 | 0.0025 | 0.0000 | 0.0000 |
|  | CuAA2 | 0.0000 | 0.0000 | 0.0025 | 0.0000 |
|  | DMETU | 6.00 | 6.00 | 6.00 | 6.00 |
|  | METU | 0.00 | 0.00 | 0.00 | 0.00 |
|  | DEETU | 0.00 | 0.00 | 0.00 | 0.00 |
|  | DMPTU | 0.00 | 0.00 | 0.00 | 0.00 |
|  | CPPTU | 0.00 | 0.00 | 0.00 | 0.00 |
|  | CQ | 0.150 | 0.150 | 0.150 | 0.150 |
|  | BHT | 0.0500 | 0.0500 | 0.0500 | 0.0500 |

TABLE 2-continued

|  |  |  |  |  |
|---|---|---|---|---|
| Monomer composition B | 42.0 | 38.0 | 38.0 | 38.0 |
| 8235 | 57.0 | 61.0 | 61.0 | 61.0 |
| Ar380 | 1.00 | 1.00 | 1.00 | 1.00 |
| Solubility of thiourea in polymerizable monomer | A | A | A | A |
| Adhesive properties to enamel (MPa) (initial) Tensile bond strength | 21.6 | 20.0 | 19.6 | 18.3 |
| Adhesive properties to dentin (MPa) (initial) Tensile bond strength | 19.8 | 19.1 | 17.7 | 15.2 |
| Working time at 23° C. (min.) (initial) | 3.5 | 3.7 | 1.4 | 7.7 |
| Working time at 23° C. (min.) (after storage at 50° C. for 2 weeks) | 3.6 | 3.8 | 1.8 | 8.6 |
| Working time at 23° C. (min.) (after storage at 50° C. for 4 weeks) | 3.5 | 3.6 | 1.9 | 7.6 |
| Curing time at 37° C. (min.) (initial) | 2.9 | 2.5 | 1.8 | 3.8 |
| Curing time at 37° C. (min.) (after storage at 50° C. for 2 weeks) | 2.8 | 2.4 | 1.8 | 4.2 |
| Curing time at 37° C. (min.) (after storage at 50° C. for 4 weeks) | 3.0 | 2.5 | 2.1 | 3.9 |
| Flexural strength of cured product of paste (MPa) | 132 | 104 | 113 | 99 |
| Flexural modulus of cured product of paste (GPa) | 6.4 | 5.3 | 4.9 | 4.2 |
| Transparency of cured product of paste (ΔL*) | 40.4 | 41.5 | 40.9 | 41.2 |
| In-water discoloration of cured product of paste (ΔE*) (after storage at 70° C. for 4 weeks) | 5.7 | 2.3 | 1.9 | 1.8 |
| Working time in contact with primer at 35° C. (sec.) | 70 | 70 | 70 | 80 |

TABLE 3

|  |  | Ex. 10 | Ex. 11 | Ex. 12 | Ex. 13 | Ex. 14 | Ex. 15 | Ex. 16 | Ex. 17 |
|---|---|---|---|---|---|---|---|---|---|
| Primer |  | P001 | P001 | P001 |  |  |  | P002 | P004 |
| MDP |  | 15.0 | 15.0 | 15.0 |  |  |  | 15.0 | 15.0 |
| #801 |  | 15.0 | 15.0 | 15.0 |  |  |  | 15.0 | 15.0 |
| HEMA |  | 35.0 | 35.0 | 35.0 |  |  |  | 35.0 | 35.0 |
| H$_2$O |  | 32.0 | 32.0 | 32.0 |  |  |  | 32.0 | 32.0 |
| VOAA |  | 0.300 | 0.300 | 0.300 |  |  |  | 0.00 | 0.00 |
| BMOV |  | 0.00 | 0.00 | 0.00 |  |  |  | 0.300 | 0.00 |
| CuAA2 |  | 0.00 | 0.00 | 0.00 |  |  |  | 0.00 | 0.0100 |
| BHT |  | 1.50 | 1.50 | 1.50 |  |  |  | 1.50 | 1.50 |
| DMAEMA |  | 2.70 | 2.70 | 2.70 |  |  |  | 2.70 | 2.70 |
| Paste A |  | A002 | A003 | A004 | A002 | A003 | A004 | A001 | A001 |
| Monomer composition A | BisGMA | 36.0 | 36.0 | 36.0 | 36.0 | 36.0 | 36.0 | 36.0 | 36.0 |
|  | D2.6E | 35.0 | 31.0 | 26.0 | 35.0 | 31.0 | 26.0 | 37.0 | 37.0 |
|  | 3G | 17.0 | 17.0 | 17.0 | 17.0 | 17.0 | 17.0 | 17.0 | 17.0 |
|  | #801 | 10.0 | 10.0 | 10.0 | 10.0 | 10.0 | 10.0 | 10.0 | 10.0 |
|  | MDP | 1.00 | 5.00 | 10.0 | 1.00 | 5.00 | 10.0 | 0.00 | 0.00 |
|  | THP | 2.00 | 2.00 | 2.00 | 2.00 | 2.00 | 2.00 | 4.00 | 4.00 |
|  | JJA | 0.225 | 0.225 | 0.225 | 0.225 | 0.225 | 0.225 | 0.225 | 0.225 |
|  | TN326 | 0.225 | 0.225 | 0.225 | 0.225 | 0.225 | 0.225 | 0.225 | 0.225 |
|  | BHT | 0.0500 | 0.0500 | 0.0500 | 0.0500 | 0.0500 | 0.0500 | 0.0500 | 0.0500 |
| Monomer composition A |  | 38.0 | 38.0 | 38.0 | 38.0 | 38.0 | 38.0 | 38.0 | 38.0 |
| 8235 |  | 51.0 | 51.0 | 51.0 | 51.0 | 51.0 | 51.0 | 51.0 | 51.0 |
| G018-117 |  | 10.0 | 10.0 | 10.0 | 10.0 | 10.0 | 10.0 | 10.0 | 10.0 |
| Ar380 |  | 1.00 | 1.00 | 1.00 | 1.00 | 1.00 | 1.00 | 1.00 | 1.00 |
| Paste B |  | B001 | B001 | B001 | B001 | B001 | B001 | B001 | B001 |
| Monomer composition B | BisGMA | 15.0 | 15.0 | 15.0 | 15.0 | 15.0 | 15.0 | 15.0 | 15.0 |
|  | D2.6E | 70.0 | 70.0 | 70.0 | 70.0 | 70.0 | 70.0 | 70.0 | 70.0 |
|  | #801 | 15.0 | 15.0 | 15.0 | 15.0 | 15.0 | 15.0 | 15.0 | 15.0 |
|  | VOAA | 0.100 | 0.100 | 0.100 | 0.100 | 0.100 | 0.100 | 0.100 | 0.100 |
|  | DMETU | 6.00 | 6.00 | 6.00 | 6.00 | 6.00 | 6.00 | 6.00 | 6.00 |
|  | CQ | 0.150 | 0.150 | 0.150 | 0.150 | 0.150 | 0.150 | 0.150 | 0.150 |
|  | BHT | 0.0500 | 0.0500 | 0.0500 | 0.0500 | 0.0500 | 0.0500 | 0.0500 | 0.0500 |
| Monomer composition B |  | 38.0 | 38.0 | 38.0 | 38.0 | 38.0 | 38.0 | 38.0 | 38.0 |
| 8235 |  | 61.0 | 61.0 | 61.0 | 61.0 | 61.0 | 61.0 | 61.0 | 61.0 |
| Ar380 |  | 1.00 | 1.00 | 1.00 | 1.00 | 1.00 | 1.00 | 1.00 | 1.00 |
| Solubility of thiourea in polymerizable monomer |  | A | A | A | A | A | A | A | A |
| Adhesive properties to enamel (MPa) (initial) Tensile bond strength |  | 22.7 | 21.7 | 17.2 | 10.2 | 13.6 | 13.8 | 17.8 | 15.7 |
| Adhesive properties to dentin (MPa) (initial) Tensile bond strength |  | 18.9 | 26.1 | 17.9 | 8.0 | 9.0 | 9.9 | 17.2 | 13.5 |
| Working time at 23° C. (min.) (initial) |  | 1.8 | 2.1 | 2.1 | 1.8 | 2.1 | 2.1 | 5.7 | 5.7 |
| Working time at 23° C. (min.) (after storage at 50° C. for 2 weeks) |  | 1.9 | 2.3 | 2.2 | 1.9 | 2.3 | 2.2 | 6.0 | 6.0 |
| Working time at 23° C. (min.) (after storage at 50° C. for 4 weeks) |  | 2.3 | 2.5 | 2.4 | 2.3 | 2.5 | 2.4 | 5.8 | 5.8 |
| Curing time at 37° C. (min.) (initial) |  | 2.0 | 2.1 | 2.1 | 2.0 | 2.1 | 2.1 | 3.0 | 3.0 |
| Curing time at 37° C. (min.) (after storage at 50° C. for 2 weeks) |  | 2.3 | 2.2 | 2.4 | 2.3 | 2.2 | 2.4 | 2.9 | 2.9 |
| Curing time at 37° C. (min.) (after storage at 50° C. for 4 weeks) |  | 2.5 | 2.1 | 2.3 | 2.5 | 2.1 | 2.3 | 3.1 | 3.1 |

TABLE 3-continued

|  | Ex. 10 | Ex. 11 | Ex. 12 | Ex. 13 | Ex. 14 | Ex. 15 | Ex. 16 | Ex. 17 |
|---|---|---|---|---|---|---|---|---|
| Flexural strength of cured product of paste (MPa) | 106 | 104 | 112 | 106 | 104 | 112 | 122 | 122 |
| Flexural modulus of cured product of paste (GPa) | 5.4 | 5.2 | 5.2 | 5.4 | 5.2 | 5.2 | 5.6 | 5.6 |
| Transparency of cured product of paste ($\Delta L^*$) | 41.0 | 39.8 | 39.6 | 41.0 | 39.8 | 39.6 | 40.8 | 40.8 |
| In-water discoloration of cured product of paste ($\Delta E^*$) (after storage at 70° C. for 4 weeks) | 4.5 | 5.5 | 6.1 | 4.5 | 5.5 | 6.1 | 4.2 | 4.2 |
| Working time in contact with primer at 35° C. (sec.) | 50 | 40 | 30 | No need for primer (Unable to perform the test) | No need for primer (Unable to perform the test) | No need for primer (Unable to perform the test) | 80 | 70 |

TABLE 4

|  |  | Com. Ex. 1 | Com. Ex. 2 | Com. Ex. 3 | Com. Ex. 4 | Com. Ex. 5 |
|---|---|---|---|---|---|---|
| Primer |  | P001 | P001 | P001 | P001 |  |
| MDP |  | 15.0 | 15.0 | 15.0 | 15.0 |  |
| #801 |  | 15.0 | 15.0 | 15.0 | 15.0 |  |
| HEMA |  | 35.0 | 35.0 | 35.0 | 35.0 |  |
| H$_2$O |  | 32.0 | 32.0 | 32.0 | 32.0 |  |
| VOAA |  | 0.300 | 0.300 | 0.300 | 0.300 |  |
| BHT |  | 1.50 | 1.50 | 1.50 | 1.50 |  |
| DMAEMA |  | 2.70 | 2.70 | 2.70 | 2.70 |  |
| Paste A |  | A001 | A001 | A001 | A001 | A003 |
| Monomer composition A | BisGMA | 36.0 | 36.0 | 36.0 | 36.0 | 36.0 |
|  | D2.6E | 37.0 | 37.0 | 37.0 | 37.0 | 31.0 |
|  | 3G | 17.0 | 17.0 | 17.0 | 17.0 | 17.0 |
|  | #801 | 10.0 | 10.0 | 10.0 | 10.0 | 10.0 |
|  | MDP | 0.00 | 0.00 | 0.00 | 0.00 | 5.00 |
|  | THP | 4.00 | 4.00 | 4.00 | 4.00 | 2.00 |
|  | JJA | 0.225 | 0.225 | 0.225 | 0.225 | 0.225 |
|  | TN326 | 0.225 | 0.225 | 0.225 | 0.225 | 0.225 |
|  | BHT | 0.0500 | 0.0500 | 0.0500 | 0.0500 | 0.0500 |
| Monomer composition A |  | 38.0 | 38.0 | 38.0 | 38.0 | 38.0 |
| 8235 |  | 51.0 | 51.0 | 51.0 | 51.0 | 51.0 |
| G018-117 |  | 10.0 | 10.0 | 10.0 | 10.0 | 10.0 |
| Ar380 |  | 1.00 | 1.00 | 1.00 | 1.00 | 1.00 |
| Paste B |  | B010 | B011 | B012 | B013 | B014 |
| Monomer composition B | BisGMA | 15.0 | 15.0 | 15.0 | 15.0 | 15.0 |
|  | D2.6E | 70.0 | 70.0 | 70.0 | 70.0 | 70.0 |
|  | #801 | 15.0 | 15.0 | 15.0 | 15.0 | 15.0 |
|  | VOAA | 0.135 | 0.100 | 0.100 | 0.100 | 0.100 |
|  | EtTU | 6.00 (Partially insoluble) | 0.00 | 0.00 | 0.00 | 6.00 (Partially insoluble) |
|  | PrTU | 0.00 | 6.00 (Partially insoluble) | 0.00 | 0.00 | 0.00 |
|  | BzTU | 0.00 | 0.00 | 6.00 (Partially insoluble) | 0.00 | 0.00 |
|  | TMTU | 0.00 | 0.00 | 0.00 | 6.00 | 0.00 |
|  | CQ | 0.150 | 0.150 | 0.150 | 0.150 | 0.150 |
|  | BHT | 0.0500 | 0.0500 | 0.0500 | 0.0500 | 0.0500 |
| Monomer composition B |  | 38.0 | 38.0 | 38.0 | 38.0 | 38.0 |
| 8235 |  | 61.0 | 61.0 | 61.0 | 61.0 | 61.0 |
| Ar380 |  | 1.00 | 1.00 | 1.00 | 1.00 | 1.00 |
| Solubility of thiourea in polymerizable monomer |  | C | C | B | A | C |
| Adhesive properties to enamel (MPa) (initial) Tensile bond strength |  | 14.4 | 11.1 | 13.5 | Uncured (Unable to perform the test) | 4.2 |
| Adhesive properties to dentin (MPa) (initial) Tensile bond strength |  | 11.9 | 10.2 | 11.0 | Uncured (Unable to perform the test) | 1.2 |
| Working time at 23° C. (min.) (initial) |  | 5.3 | 5.8 | 5.9 | Uncured for at least 15 minutes | 4.3 |
| Working time at 23° C. (min.) (after storage at 50° C. for 2 weeks) |  | 8.3 | 9.2 | 15.5 | Uncured for at least 15 minutes | 7.8 |
| Working time at 23° C. (min.) (after storage at 50° C. for 4 weeks) |  | 10.8 | 11.5 | 18.0 | Uncured for at least 15 minutes | 9.4 |
| Curing time at 37° C. (min.) (initial) |  | 3.2 | 3.1 | 3.5 | Uncured for at least 15 minutes | 2.3 |
| Curing time at 37° C. (min.) (after storage at 50° C. for 2 weeks) |  | 4.3 | 4.4 | 5.7 | Uncured for at least 15 minutes | 3.9 |
| Curing time at 37° C. (min.) (after storage at 50° C. for 4 weeks) |  | 5.6 | 5.9 | 6.8 | Uncured for at least 15 minutes | 4.8 |

TABLE 4-continued

| | Com. Ex. 1 | Com. Ex. 2 | Com. Ex. 3 | Com. Ex. 4 | Com. Ex. 5 |
|---|---|---|---|---|---|
| Flexural strength of cured product of paste (MPa) | 121 | 87 | 133 | Uncured (Unable to perform the test) | 100 |
| Flexural modulus of cured product of paste (GPa) | 5.2 | 3.7 | 7.0 | Uncured (Unable to perform the test) | 4.8 |
| Transparency of cured product of paste (ΔL*) | 43.1 | 41.2 | 42.5 | Uncured (Unable to perform the test) | 41.0 |
| In-water discoloration of cured product of paste (ΔE*) (after storage at 70° C. for 4 weeks) | 2.2 | 2.8 | 2.5 | Uncured (Unable to perform the test) | 5.2 |
| Working time in contact with primer at 35° C. (sec.) | 70 | 70 | 70 | Uncured for at least 300 seconds | No need for primer (Unable to perform the test) |

INDUSTRIAL APPLICABILITY

The curable composition and adhesive kit of the present invention are suitable for use in dental applications, and are best suited, in particular, as a dental cement and a dental cement kit, respectively.

The invention claimed is:

1. A curable composition (A), comprising:
    a radical polymerizable monomer (a1) having no acidic group;
    a hydroperoxide compound (a2); and
    at least one cyclic thiourea compound (a3) selected from the group consisting of a substituted ethylenethiourea compound (a3-1), a substituted propylenethiourea compound (a3-2), and a substituted butylenethiourea compound (a3-3),
    wherein
    the substituted ethylenethiourea compound (a3-1) has a structure represented by the following formula (I):

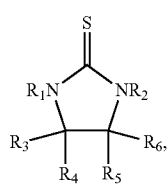

(I)

where $R_1$, $R_2$, $R_3$, $R_4$, $R_5$, and $R_6$ are each independently a hydrogen atom, an optionally substituted alkyl group, an optionally substituted cycloalkyl group, an optionally substituted alkoxy group, an optionally substituted aryl group, an optionally substituted acyl group, an optionally substituted alkenyl group, an optionally substituted aralkyl group, or an optionally substituted monovalent heterocyclic group containing an oxygen atom, a sulfur atom or a nitrogen atom, provided that all of $R_1$, $R_2$, $R_3$, $R_4$, $R_5$, and $R_6$ are not simultaneously hydrogen atoms, the substituted propylenethiourea compound (a3-2) has a structure represented by the following formula (II):

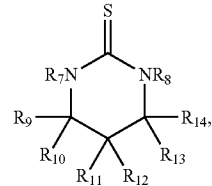

(II)

where $R_7$, $R_8$, $R_9$, $R_{10}$, $R_{11}$, $R_{12}$, $R_{13}$, and $R_{14}$ are each independently a hydrogen atom, an optionally substituted alkyl group, an optionally substituted cycloalkyl group, an optionally substituted alkoxy group, an optionally substituted aryl group, an optionally substituted acyl group, an optionally substituted alkenyl group, an optionally substituted aralkyl group, or an optionally substituted monovalent heterocyclic group containing an oxygen atom, a sulfur atom or a nitrogen atom, provided that all of $R_7$, $R_8$, $R_9$, $R_{10}$, $R_{11}$, $R_{12}$, $R_{13}$, and $R_{14}$ are not simultaneously hydrogen atoms and that $R_9$ and $R_{11}$, or $R_9$ and $R_{13}$, together with carbon atoms to which $R_9$ and $R_{11}$, or $R_9$ and $R_{13}$ are attached, may form an optionally substituted ring, and the substituted butylenethiourea compound (a3-3) has a structure represented by the following formula (III):

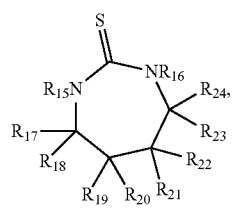

(III)

where $R_{15}$, $R_{16}$, $R_{17}$, $R_{18}$, $R_{19}$, $R_{20}$, $R_{21}$, $R_{22}$, $R_{23}$, and $R_{24}$ are each independently a hydrogen atom, an optionally substituted alkyl group, an optionally substituted cycloalkyl group, an optionally substituted alkoxy group, an optionally substituted aryl group, an optionally substituted acyl group, an optionally substituted alkenyl group, an optionally substituted aralkyl group, or an optionally substituted monovalent heterocyclic group containing an oxygen atom, a sulfur atom or a nitrogen atom, provided that all of $R_{15}$, $R_{16}$, $R_{17}$, $R_{18}$, $R_{19}$, $R_{20}$, $R_{21}$, $R_{22}$, $R_{23}$, and $R_{24}$ are not simultaneously hydrogen atoms and that $R_{17}$ and $R_{19}$, $R_{17}$ and $R_{21}$, $R_{17}$ and $R_{23}$, or $R_{19}$ and $R_{21}$, together with carbon atoms to which $R_{17}$ and $R_{19}$, $R_{17}$ and $R_{21}$, $R_{17}$ and $R_{23}$, or $R_{19}$ and $R_{21}$ are attached, may form an optionally substituted ring.

2. The curable composition (A) according to claim 1, further comprising a filler (a4).

3. The curable composition (A) according to claim 1, wherein the radical polymerizable monomer (a1) having no acidic group is a (meth)acrylate polymerizable monomer and/or a (meth)acrylamide polymerizable monomer.

4. The curable composition (A) according to claim 1, further comprising an acidic group-containing radical polymerizable monomer (a5).

5. The curable composition (A) according to claim 1, further comprising a vanadium compound (a6) and/or a copper compound (a7).

6. The curable composition (A) according to claim 1, wherein the cyclic thiourea compound (a3) is at least one selected from the group consisting of 4-methyl-2-imidazolidinethione, 4,4-dimethyl-2-imidazolidinethione, 4-ethyl-2-imidazolidinethione, and 4,4-diethyl-2-imidazolidinethione.

7. A dental method, comprising:
applying the curable composition (A) according to claim 1 to a tooth structure.

8. An adhesive kit comprising:
a pretreatment agent (B) comprising an acidic group-containing radical polymerizable monomer (b1), a polymerization accelerator (b2), a solvent (b3), and a hydrophilic radical polymerizable monomer (b4) having no acidic group; and
the curable composition (A) according to claim 1.

9. The adhesive kit according to claim 8, wherein the polymerization accelerator (b2) is a vanadium compound (b2-1) and/or a copper compound (b2-2).

10. A dental method, comprising:
applying the pretreatment agent (B) and the curable composition (A) of the adhesive kit according to claim 8 to a tooth structure.

11. The curable composition (A) according to claim 1, wherein the at least one cyclic thiourea compound (a3) comprises the substituted ethylenethiourea compound (a3-1) and
the substituted ethylenethiourea compound (a3-1) is 4,4-dimethyl-2-imidazolidinethione.

12. The curable composition (A) according to claim 1, wherein the at least one cyclic thiourea compound (a3) comprises the substituted propylenethiourea compound (a3-2) and
the substituted propylenethiourea compound (a3-2) is 5,5-dimethyl-3,4,5,6-tetrahydropyrimidine-2(1H)-thione.

13. The curable composition (A) according to claim 1, wherein the at least one cyclic thiourea compound (a3) is selected from the group consisting of the substituted propylenethiourea compound (a3-2) and the substituted butylenethiourea compound (a3-3).

* * * * *